United States Patent [19]
Hui et al.

[11] Patent Number: 5,817,766
[45] Date of Patent: Oct. 6, 1998

[54] REAGENTS FOR A CANNABINOID IMMUNOASSAY

[75] Inventors: Raymond Albert Hui, Lyndhurst; Steven Mark Rosen, Bloomfield; Salvatore Joseph Salmone, Stockton, all of N.J.

[73] Assignee: Roche Diagnostic Systems, Inc., Branchburg, N.J.

[21] Appl. No.: 417,331

[22] Filed: Apr. 5, 1995

[51] Int. Cl.$^6$ .......................... C07K 16/00; C07K 17/00; C07D 311/04
[52] U.S. Cl. ...................... 530/387.1; 530/338.9; 530/389.8; 422/61; 549/401; 549/404; 549/405; 549/408; 548/425
[58] Field of Search ...................... 549/401, 404, 549/405, 408; 530/403–405, 408–410, 387.1, 388.9, 389.8; 436/543, 544; 422/61; 548/525

[56] References Cited

U.S. PATENT DOCUMENTS

| | | |
|---|---|---|
| 4,329,281 | 5/1982 | Christenson et al. . |
| 4,438,207 | 3/1984 | Fahrenholtz et al. . |
| 4,833,073 | 5/1989 | McNally et al. . |
| 5,144,030 | 9/1992 | Wang et al. . |
| 5,223,441 | 6/1993 | Ullman et al. . |
| 5,237,057 | 8/1993 | Buechler et al. . |
| 5,264,373 | 11/1993 | Wang et al. . |
| 5,315,015 | 5/1994 | Hui et al. ................ 549/223 |

FOREIGN PATENT DOCUMENTS

| | | |
|---|---|---|
| 02/57177 | 8/1988 | Japan . |
| 02/57178 | 8/1988 | Japan . |
| 02/101072 | 10/1988 | Japan . |
| 03/46562 | 7/1989 | Japan . |

*Primary Examiner*—Ponnathapura Achutamurthy
*Attorney, Agent, or Firm*—George W. Johnston; Patricia S. Rocha-Tramaloni

[57] ABSTRACT

Novel benzpyran derivatives and the use of these derivatives in producing novel anti-cannabinoid antibodies are disclosed. Also disclosed is the use of these antibodies as reagents in improved immunoassays for tetrahydrocannabinol metabolites in biological fluid samples.

22 Claims, 2 Drawing Sheets

REAGENTS FOR A CANNABINOID IMMUNOASSAY

TECHNICAL FIELD

This invention relates to novel benzpyran derivatives and to the use of these derivatives in producing anti-cannabinoid antibodies and to the use of these antibodies as reagents in improved immunoassays for tetrahydrocannabinol metabolites in biological fluid samples.

BACKGROUND OF THE INVENTION

Increases in the use of marijuana have led to the development of assays for the detection of the primary active constituent of the marijuana plant, $\Delta^9$-tetrahydrocannabinol (THC) and, more particularly, metabolites of THC in urine and blood samples. The most common commercial assays employ the use of labeled cannabinoid derivatives in conjunction with antibodies against metabolites of the drug.

In practice, a blood or urine sample suspected of containing tetrahydrocannabinol metabolites (including glucuronides and other conjugation products) is contacted with antibodies in the presence of a labeled cannabinoid derivative. To the extent that tetrahydrocannabinol metabolites are present in the sample, there will be competition for binding to the combining sites of the antibodies, and the amount of the labeled derivative that remains bound will be reduced in proportion to the degree of competition with tetrahydrocannabinol metabolites in the sample.

Descriptions of some representative immunoassays are provided in O'Connor et al., J. Anal. Toxicol. 5:168 (1981), Law et al., J. Anal. Toxicol. 8:14 (1984), Childs et al., J. Anal. Toxicol. 8:220 (1984), and U.S. Pat. No. 4,833,073. In all of these references, it is the displacement of some of the labeled cannabinoid derivative by metabolites in the assay samples that is the basis of the assays described. The best assay results are obtained when the labeled derivative is specifically recognized by the antibodies and yet is easily displaced by the various products of tetrahydrocannabinol metabolism.

Anti-cannabinoid antibodies that have broad specificity for tetrahydrocannabinol metabolites are highly desirable for use in these immunoassays. The antibody should be able to recognize as many of the major metabolites as possible. Additionally, it should recognize the parent compound itself.

SUMMARY OF THE INVENTION

The present invention relates to novel benzpyran derivatives having the formula

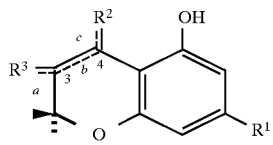

where $R^1$ is a linear or branched alkyl group having from 1 to 9 carbon atoms; $R^2$ and $R^3$ are independently selected from linear or branched lower alkyl which can be substituted by one or more of the following functional groups —OH, —COR$^4$, —NR$^5$R$^6$, —SH, —C(=NH)—OR$^7$, —CHO, or =O, provided that at least one of $R^2$ or $R^3$ is substituted by at least one of the above-described functional groups; $R^4$ is —OH or a leaving group; $R^5$ and $R^6$ are independently selected from the group consisting of H, and linear or branched lower alkyl; $R^7$ is linear or branched lower alkyl; and a, b, and c are independently single or double bonds, provided that when b is a double bond, then a and c are not double bonds.

This invention further relates to the use of the above compounds in producing novel antibodies against tetrahydrocannabinol metabolites and the use of these novel antibodies in immunoassays for the detection of tetrahydrocannabinol metabolites in blood or urine samples, and to methods for producing the novel antibodies.

Conventional immunization strategies that utilize a single THC immunogen tend to produce antibodies that are more selective in their cross-reactivity. In general, such strategies are directed toward the detection of the most important metabolite, namely $\Delta^9$-11-nor-9-carboxy-THC ($\Delta^9$-THC acid)

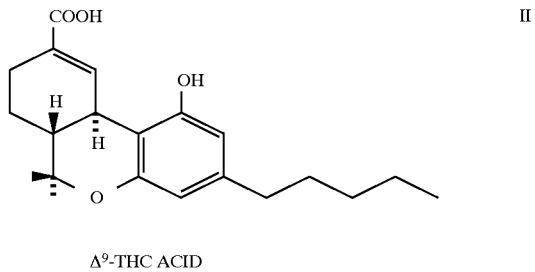

$\Delta^9$-THC ACID

In cases where broader cross-reactivities have been desired for the detection of THC metabolites, such as would be the case for use in an immunoassay, the traditional approach to achieve such broader cross-reactivities has been to generate polyclonal responses in an animal to a single immunogen. Such an approach, however, does not lead to broadly cross-reacting antibodies as a matter of expectation but merely increases the chances of obtaining such antibodies.

In contrast to polyclonal antibodies, monoclonal antibodies tend to be very specific in their recognition of molecules (antigens). This property of monoclonal antibodies creates difficulty in cases where one wishes to create monoclonal antibodies capable of recognizing a wide range of similar but not identical compounds such as is the case in the detection of THC metabolites. The present invention solves this problem by providing, inter alia, monoclonal antibodies that recognize the major metabolites of THC.

BRIEF DESCRIPTION OF THE FIGURES

The present invention may be more readily understood by reference to the following figures, in which.

DETAILED DESCRIPTION OF THE INVENTION

Figure 1:
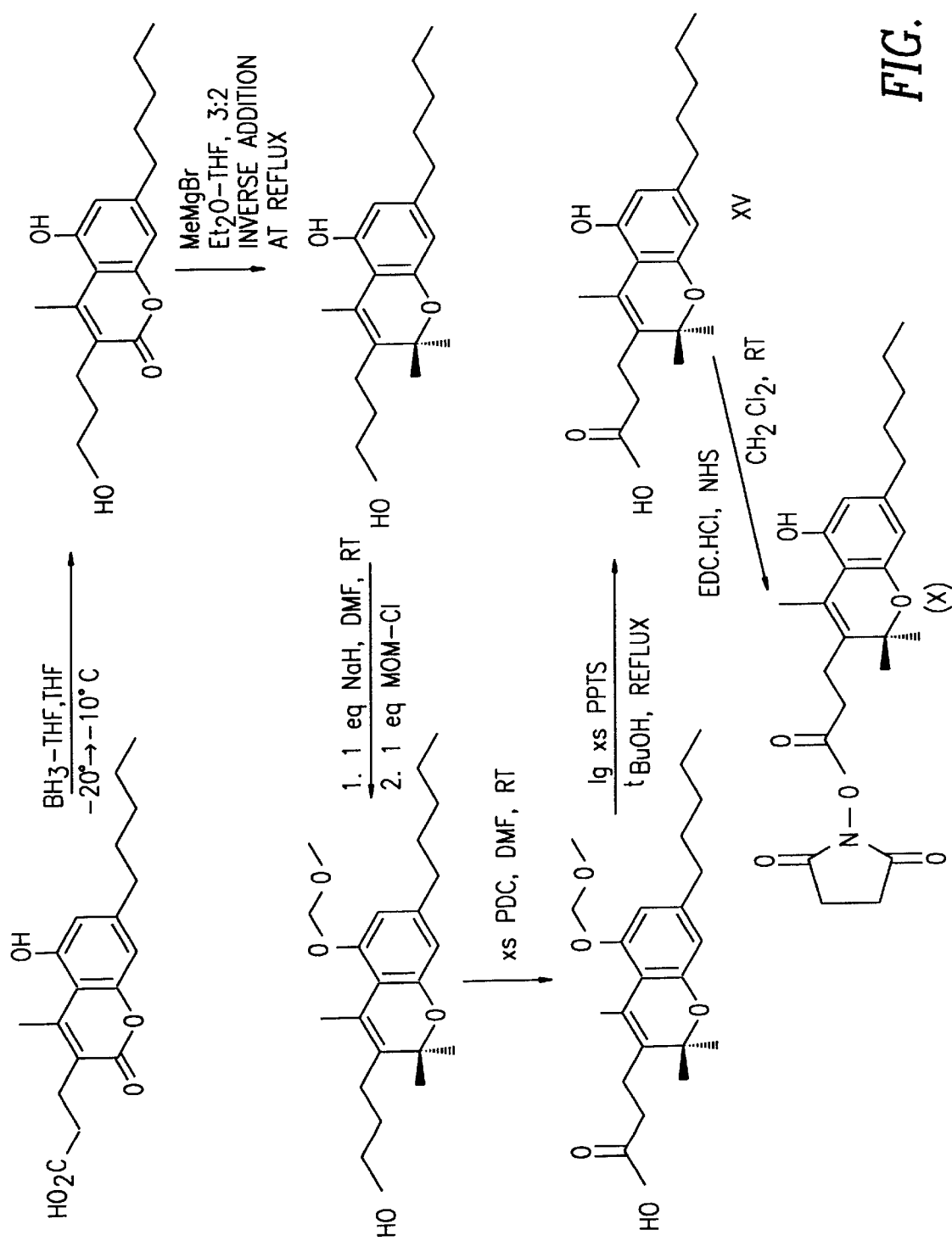
FIG. 1 shows the formulae of the starting materials and intermediates involved in the synthesis of 1-[3-(5-Hydroxy-2,2,4-trimethyl-7-pentyl-2H-1-benzopyran-3-yl)-1-oxopropoxy]-2,5-pyrrolidinedione (compound X), as well as compound XV.

In contrast to normal expectations, by using the novel immunogens taught herein and a successive immunization strategy as is further described below, we were able to produce anti-cannabinoid monoclonal, as well as polyclonal, antibodies that were highly cross-reactive not only to the most important THC metabolite (Formula II), but also to the other major metabolites of THC. This is unexpected in that we have manipulated the polyclonal response of the mouse to derive individual monoclonal antibodies that have broader cross-reactivity to all the major THC metabolites than has previously been achieved with polyclonal antibodies. We have also obtained polyclonal antibodies with better cross-reactivity to the THC metabolites than those previously disclosed.

The activity and superiority of the novel antibodies disclosed herein have been tested and proven in commercial immunoassays for THC metabolites (Table 2) as well as with clinical specimens (Table 3).

The novel method for immunization described herein can be broadly applied in the development of any antibody where increased cross-reactivity to multiple, structurally related epitopes is desired.

As used herein, "lower alkyl" shall mean linear or branched chain, saturated or unsaturated, $C_1$–$C_6$ alkyl, such as methyl, ethyl, propyl, isopropyl, methylene, ethenyl, propenyl, etc.

A "leaving group" is a group that can be displaced or cleaved, for example by a suitable nucleophile. Such leaving groups and the conditions for their displacement, are well known to those skilled in the art. See e.g., J. March, *Advanced Organic Chemistry*, pp 179 and pp. 310–316 (1985). In general, the leaving groups $R^4$ of interest in the present invention are those wherein the point of attachment to the carbonyl of the functional group —$COR^4$ is through a heteroatom, such as for example, O, N, or S. Sample leaving groups which are readily displaced by a suitable nucleophile include N-oxysuccinimide, N-oxy (sulfosuccinimide), imidazolyl, pentafluorophenoxy, N-oxybenztriazole, and thio(oxo)thiazolidinyl. Additionally, leaving groups within the teaching of the instant invention include —$OR^8$ wherein $R^8$ is a linear or branched lower alkyl group (these are commonly known as alkyl esters), whose displacement or cleavage may be effected by somewhat more rigorous conditions than for the immediately preceding leaving groups. These more rigorous conditions are also well-known in the art. See, e.g., March supra.

The major metabolites of THC other than $\Delta^9$—THC acid (II) are:

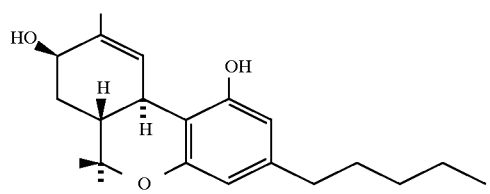

8β-OH-$\Delta^9$-THC (III)

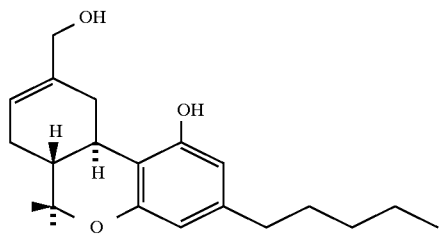

11-OH-$\Delta^8$-THC (IV)

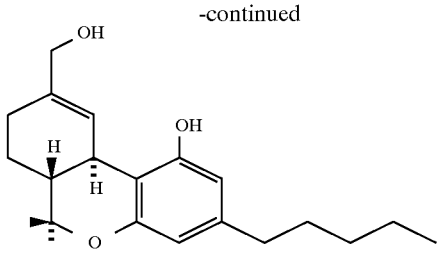

11-OH-$\Delta^9$-THC (V)

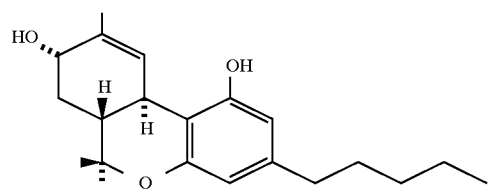

8α-OH-$\Delta^9$-THC (VI)

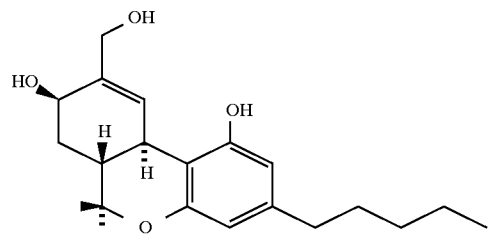

8β, 11-diOH-$\Delta^9$-THC (VII)

As is shown by the structure of these metabolites, most of the metabolism of the parent molecule occurs at position 8, or the methyl group attached to position 9. Additional metabolism also occurs on the n-pentyl chain attached to the benzene ring. Little of the metabolism of THC occurs at the benzpyran-like core portion of the molecule which is common to all the major THC metabolites. Additionally, many of the THC metabolites are excreted as glucuronides, especially when conjugated at position 1 (the phenolic position) or positions 8 or 9 (especially with metabolite II). Metabolites carrying a glucuronide at position 1 are classified as metabolized at position 1.

When a cannabinoid compound is covalently conjugated to a carrier protein for the purposes of making an immunogen, the site of linkage on the cannabinoid molecule to the carrier protein will determine the specificity of the resulting antibodies. When the carrier is conjugated to a cannabinoid compound through position 9 of the drug, the epitope(s) that exist at that position will be blocked from detection by the immune system. Antibodies to metabolites that have been metabolized at position 9 are less likely to be generated because the B cells of the immune system, whose antigen-specific receptors would otherwise be stimulated by this portion of the cannabinoid molecule, are prevented from being stimulated by steric hindrance at that position. The position 1 epitopes will be available to be recognized by the immune system and antibodies to the position 1 subclass of metabolites will be generated.

Similarly, when the carrier is linked to drug through position 1, the epitope(s) that exist at position 1 are less capable of being recognized by the immune system for the same reasons as given above. Antibodies to the position 1 associated metabolites are less likely to be generated from the position 1 cannabinoid conjugated immunogen. Furthermore, the position 9 epitopes will be available to be recognized by the immune system and antibodies to the position 9 subclass of metabolites are more likely to be generated.

In one embodiment of the present invention, we have developed novel THC-derivatives retaining the benzpyran core of the cannabinoid/THC molecule. These basic molecules are then used to create immunogens which in turn are used to generate cross-reactive antibodies with high affinity for all the major metabolites of THC.

The benzpyran derivatives of the present invention have the structure

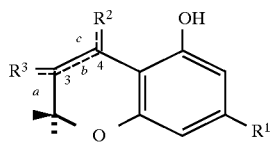
(I)

where $R^1$ is a linear or branched alkyl group having from 1 to 9 carbon atoms; $R^2$ and $R^3$ are independently selected from linear or branched lower alkyl which can be substituted by one or more of the following functional groups —OH, —COR$^4$, —NR$^5$R$^6$, —SH, —C(=NH)—OR$^7$, —CHO, or =O, provided that at least one of $R^2$ or $R^3$ is substituted by at least one of the above-described functional groups; $R^4$ is —OH or a leaving group; $R^5$ and $R^6$ are independently selected from the group consisting of H, and linear or branched lower alkyl; $R^7$ is linear or branched lower alkyl; and a, b, and c are independently single or double bonds, provided that when b is a double bond, then a and c are not double bonds.

In preferred embodiments, $R^1$ is linear or branched $C_3$–$C_6$; $R^2$ is —CH$_3$; $R^3$ is a linear or branched lower alkyl substituted by one or more of the functional groups —OH, —COR$^4$ and —NR$^5$R$^6$; $R^4$ is —OH or a leaving group which is selected from N-oxysuccinimide, N-oxy (sulfosuccinimide), imidazolyl, pentafluorophenoxy, N-oxybenztriazole, thio(oxo)thiazolidinyl, and —OR$^8$; $R^5$ and $R^6$ are independently H or lower alkyl, most preferably —CH$_3$ or —CH$_2$CH$_3$; $R^8$ is a linear or branched lower alkyl; and a and c are single bonds.

Most preferably $R^1$ is linear $C_3$–$C_6$; $R^2$ is —CH$_3$; $R^3$ is linear lower alkyl substituted by one or more —OH or —COR$^4$; $R^4$ is selected from the group consisting of —OH, N-oxysuccinimide and —OR$^8$; $R^8$ is selected from —CH$_3$ and —CH$_2$CH$_3$; and a and c are single bonds.

Most preferred compounds of formula I include

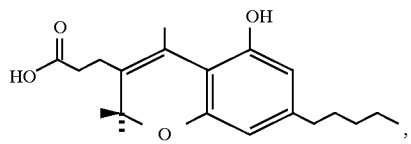
(XV)

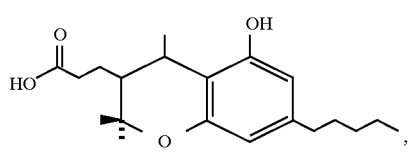
(XVI)

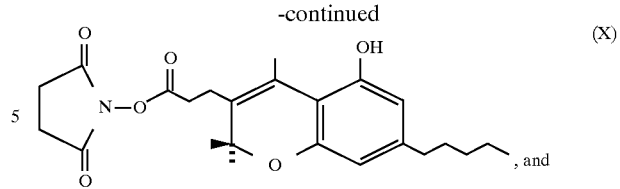
(X)

, and

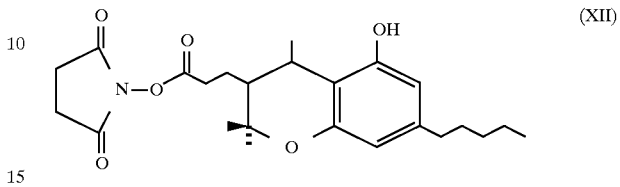
(XII)

The compounds of formula I can be prepared by methods well-known in the art of chemical synthesis. They may be obtained, for example, by the initial condensation of a suitable 5-alkyl substituted 1,3-dihydroxybenzene with a suitably further functionalized or suitably further substituted 3-ketoalkanoate ester, such as, for example, the 2-acetylalkanedioate esters exemplified by Fahrenholtz et al. in *J. Amer. Chem. Soc.*, 1967, 89, 5934–5941, or by Archer et al. in *J. Org. Chem.*, 1977, 42, 2277–2284, to give coumarins which are then further transformed at the ester functionalities, such as hydrolysis to acids or reduction to alcohols, and at the coumarin nucleus, to give substituted benzpyrans. These foregoing methods are exemplified by Fahrenholtz, supra, and by Archer, supra. Acids may then be converted to esters, including activated esters such as an N-hydroxy-succinimide esters, or to amides, such as an imidazolyl amide, by methods well-known in the art. Various 5-substituted 1,3-dihydroxybenzenes and further substituted or functionalized 3-ketoalkanoates may be used in such condensations, such as, for example, in the general method described by Fahrenholtz, supra and by Archer, supra. This approach is specifically exemplified in Examples 1, 2, 7, 8, and 9, infra.

Additionally, compounds of formula I may be obtained from chromanones, such as suitably substituted 3-chromanones (3,4-dihydro-2H-1-benzopyran-3-ones) or suitably substituted 4-chromanones (2,3-dihydro-4H-1-benzopyran-4-ones), by methods known in the art. The syntheses of 3-chromanones and 4-chromanones are well-known in the art of organic synthesis and various general methods are known for their syntheses. See, e.g., Lockhart, I. M., in "Chromenes, Chromanones, and Chromones," The Chemistry of Heterocyclic Compounds, Vol. 31, Ellis, G. P. (Ed.), John Wiley & Sons, Inc., 1977, Chapters III, IV, and V. As an illustrative example, a suitable 4-chromanone such as a 2,2-dimethyl-5-hydroxy-7-R$^1$-1-benzopyran-4-one of structure (Ib) depicted below

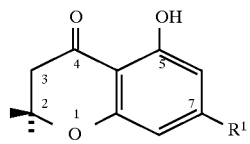
(Ib)

wherein $R^1$ has the same meanings given above (see, e.g., Fahrenholtz et al., supra; Arnoldi, in *Synthesis*, 1984, 856–859; Arnoldi et al., in *J. Med. Chem.*, 1990, 33, 2865–2869) and wherein the phenolic hydroxy is suitably protected, such as by silylation or etherification, may be alkylated at the 3-position with a suitable substituted or unsubstituted alkyl reagent by methods well-known in the art, followed by a Wittig reaction at the 4-keto group with a suitable Wittig reagent, also by methods well-known in the art, to give, after removal of the protecting groups, compounds of formula I with an exo double bond at the 4-position, that is, wherein c in formula I is a double bond.

As an alternative illustrative example, compound (Ib), wherein the phenolic hydroxy is first protected, may be condensed with a suitable alkyl aldehyde bearing additional protected substituents on the alkyl chain, by methods well-known in the art, to give a 4-chromanone bearing a substituted alkyl group at the 3-position linked through a double bond. The resulting compound may then be reacted at the 4-keto group with a suitable Wittig reagent to give, after removal of protecting groups, benzpyrans of formula I having exo double bonds at both positions 3 and 4, that is, wherein a and c in formula I are double bonds.

As a further illustrative example, a suitable 4-chromanone such as a compound of formula (Ib) above, wherein the phenolic hydroxy is suitably protected, may be reacted at the 4-keto group with a suitable alkyl organometallic reagent, such as, for example, methyllithium or the like, under conditions known in the art, to give a tertiary alcohol which may then be dehydrated to the corresponding 3,4-dehydro compound by methods known in the art. The resulting compound may then be epoxidized at the 3,4-double bond through methods known in the art, and the epoxide rearranged under catalysis by a suitable Lewis acid such as boron trifluoride etherate or the like, to give the corresponding 3-chromanone bearing an alkyl group at position 4. This compound may then be reacted at the 3-keto group with a suitable Wittig reagent followed by removal of protecting groups to give compounds of formula I bearing an exo double bond at position 3, that is, wherein a in formula I is a double bond.

The above examples are illustrative only and other alternative methods of synthesizing appropriate 3-chromanones and 4-chromanones, as well as coumarins, will be suggested to one skilled in the art of organic synthesis.

Additionally, coumarins (and hence benzpyrans) bearing an amino functionality on the substituent at C-3 or C-4 of that compound may be obtained by utilizing the corresponding amino-substituted 3-ketoalkanoate wherein the amino functionality may be protected by a suitable group or groups, such as by cyclic bissilylation, or by conversion to a suitable carbamate or amide or phthalimide. Other alternative methods of introducing an amino functionality onto the alkyl substituent at C-3 or C-4 of the coumarin or benzpyran, such as by nucleophilic substitution by an amine nucleophile of a hydroxyalkyl coumarin or benzpyran, wherein the alkyl hydroxy is activated by conversion into a leaving group, for example by conversion to a tosyl or mesyl group, is readily apparent to those skilled in the art.

Figure 2:
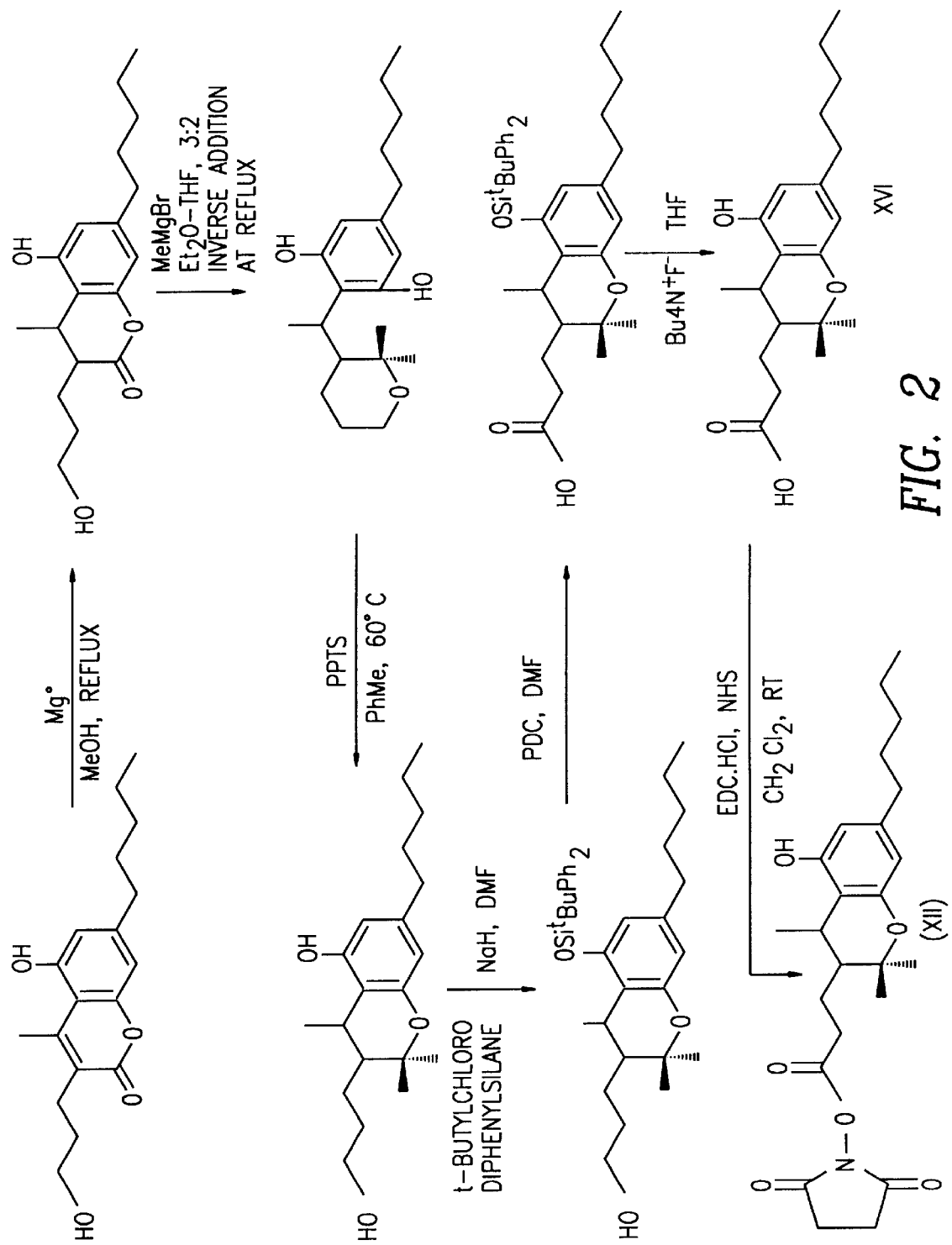
FIG. 2 shows the formulae of the starting materials and intermediates involved in the synthesis of 1-[3-(3,4-Dihydro-5-hydroxy-2,2,4-trimethyl-7-pentyl-2H-1-benzopyran-3-yl)-1-oxopropoxy]-2,5-pyrrolidinedione (compound XII), as well as compound XVI.

Conversion of coumarins to benzpyrans is also achieved by methods also known to those skilled in the art. These approaches are exemplified in FIGS. 1 and 2, infra.

Benzpyrans bearing an aldehyde (—CHO) or keto (—C(=O)—) functionality on the alkyl substituent at C-3 or C-4 of the benzpyran may be obtained from the corresponding hydroxy compound by oxidation with a suitable reagent such as pyridinium dichromate or chlorochromate in a suitable solvent such as dichloromethane, wherein the phenolic hydroxy of the benzpyran is first protected by a suitable protecting group, such as by silylation with a hindered silyl group, for example, a tert-butyldiphenylsilyl group.

Additionally, benzpyrans bearing a thiol (—SH) functionality on the substituent at C-3 or C-4 may be obtained from the corresponding hydroxyalkyl compound by methods well-known in the art, such as, for example, by reaction with thiourea followed by hydrolysis, or by activation of the hydroxy group by conversion to a tosylate or mesylate group followed by reaction with a suitable thiol nucleophile such as thioacetic acid followed by hydrolysis.

Benzpyrans bearing an imidate functionality such as —C(=NH)—OCH$_3$ or —C(=NH)—OCH$_2$CH$_3$ on the substituent at C-3 or C-4 may be obtained by treatment of the corresponding nitrile (cyano) compound with HCl gas in a suitable alcohol, such as methanol or ethanol. Such nitrites may, in turn, be obtained from the corresponding hydroxy-alkyl compounds by methods well-known in the art, such as, for example, by reaction with a cyanide such as sodium cyanide in the presence of an activating agent such as triphenylphosphine, or by activation of the hydroxy by conversion to the tosylate or mesylate followed by reaction with, for example, sodium cyanide in a suitable solvent such as DMSO or DMF. Other methods of introducing —SH or —CN (and hence —C(=NH)—OCH$_3$ or —C(=NH)—OCH$_2$CH$_3$ groups, such as by nucleophilic substitution of the corresponding halide (—Cl, or —Br, or —I) compounds, as well as interconversions between such functionalities, will be apparent to those skilled in the art of chemical synthesis.

When used as immunogens to elicit antibodies, the compounds of formula I are conjugated, optionally through a linking group, either through $R^2$ or $R^3$ with a carrier component to assist in the delivery of the immunogen to a host.

Preferred immunogens according to the present invention have the structure of formula (Ia) below

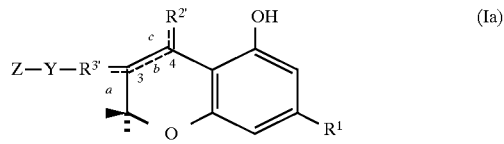

wherein $R^1$ has the meaning given above; $R^{2'}$ is linear or branched lower alkyl; $R^{3'}$ is linear or branched lower alkyl which is substituted by —O—, —CO—, —NR$^5$—, —NR$^6$—, —S—, —C(=NH)—, —CH=, —CH$_2$—; $R^5$ and $R^6$ have the meanings given above; Y is a linking group or a bond; Z is a carrier; and a, b, and c have the meanings given above.

As used herein, the term "carrier" includes those materials which have the property of independently eliciting an immunogenic response in a host animal and which can be covalently coupled to the above-described benzpyran derivative of formula (I) (the "hapten"). Suitable carrier materials include, for example, proteins; natural or synthetic polymeric compounds such as polypeptides, e.g., polylysine or copolymers of other amino acids; polysaccharides, and the like. Particularly-preferred carrier materials are proteins and polypeptides, especially proteins.

The identity of the protein materials utilized in the preparation of an immunogen of the instant invention is not critical. Examples of suitable proteins useful in the practice of this invention include mammalian serum proteins such as, for example, human gamma globulin, human serum albumin, human IgG and IgA, bovine thyroglobulin (BTG), bovine serum albumin (BSA), methylated bovine serum albumin, rabbit serum albumin, bovine gamma globulin, thyroglobulin or a haemocyanin. Other protein products will be suggested to one skilled in the art. It is generally preferred, but not necessary, that proteins be utilized which are foreign to the animal hosts in which antibodies against the cannabinoid metabolite or derivative are to be elicited.

"Carriers" are typically used because low molecular weight compounds (here, the hapten) are generally not immunogenic when administered by themselves. When a carrier is conjugated to a hapten and the conjugate is used as an immunogen, antibodies can be generated to the hapten that would not be produced by immunization with hapten alone. This is known as the "carrier effect."

"Linking groups" are known in the art and are commonly used to provide additional spacing between a hapten and the carrier molecule. Use of a linking group may or may not be advantageous or needed depending on the specific hapten and carrier pairs, and selection of an appropriate linking group is within the skill of the art. See, e.g., U.S. Pat. No. 5,144,030 (column 16, line 1, et seq.) and U.S. Pat. No. 5,237,057 (column 2). Typical linking groups will be from 1–20 carbon atoms and 0–10 heteroatoms (e.g., NH, O ,S) and may be straight or branched chain. It is well known to those skilled in the art that only combinations of atoms which are chemically compatible can comprise the linking group, e.g., permit covalent bonding with carrier and hapten.

Immunogens of formula Ia are prepared from compounds of formula I by covalent coupling to the carrier by techniques well known in the art, the exact choice of which will depend on the nature of the functional groups in the benzpyran derivative, as well as in the carrier molecule, that are available for coupling. Often, to ensure an adequate degree of coupling of a hapten (compound of formula I) under mild conditions so as to minimize deleterious effects on a proteinatious carrier, it is desirable to convert those compounds of formula I (the "hapten") wherein $R^3$ ends in an acid group (compounds of formula XV and XVI) to an isolatable activated form prior to coupling. One particularly preferred isolatable activated form of the haptenic free acid is the N-hydroxysuccinimide ester, (e.g., compounds of formulas X and XII). See U.S. Pat. No. 4,329,281, columns 2–3.

In addition, the reaction of the hapten of formula I with the carrier may be conducted with the aid of a coupling agent such as a carbodiimide. For example, a hapten bearing a carboxy substituent (e.g., compounds of formula XV and XVI) may be coupled with a protein bearing alkylamino groups such as the ε-amino groups of lysine residues in the presence of a carbodiimide which serves to activate the carboxy groups of such a hapten thereby allowing it to react with the amino groups of the protein.

Alternatively, as an illustrative example which is well-known in the art, a hapten bearing an activated carboxy group such as, but not limited to, an N-oxysuccinimidylcarboxylate, may be reacted with the ε-amino groups of the lysine residues of a protein such as thyroglobulin.

Additionally, by procedures also well-known in the art, haptens bearing an imidate group may be reacted with the ε-amino groups of the lysine residues of such proteins.

Haptens bearing an aldehyde group may be coupled directly to the ε-amino groups of the lysine residues of proteins to form imine linkages which may be stabilized by reduction to the corresponding alkylamine with a suitable borohydride such as sodium cyanoborohydride. Alternatively, haptens bearing an aldehyde group or a keto group may be coupled with a linking group, for example, a suitable alkoxyamine such as carboxymethoxylamine, to form the corresponding oxime bearing a carboxy functionality which may be activated by conversion to, for example, an N-hydroxysuccinimide ester, which may then be coupled to protein. The above-described chemical processes are also well recognized in the art of chemical synthesis.

Haptens bearing a thiol functionality may be reacted with proteins bearing thiol-reactive groups, such as maleimido groups, as is exemplified by Buechler et al. in U.S. Pat. No. 5,237,057.

The above descriptions are merely illustrative and various additional methods of coupling haptens to proteins or polypeptides are known to one skilled in the art. See, for example, U.S. Pat. No. 5,144,030 (column 16).

In another embodiment of the present invention, immunogens derived from at least one of the compounds of formula I, are used to induce the formation of ("elicit") antibodies that are specific to tetrahydrocannabinol metabolites in host animals.

Various methods are known in the art for the induction of antibodies. Discussions of, and procedures for, the synthesis of immunogens for the generation of such antibodies have been given in, for example, Wang et al., U.S. Pat. No. 5,144,030 (Abbott Labs); Fahrenholtz et al., U.S. Pat. No. 4,438,207 (Hoffmann-La Roche); NcNally et al., U.S. Pat. No. 4,833,073 (Hoffmann-La Roche); and Ullman et al., U.S. Pat. No. 5,223,441 (Syntex). For example, the host animal is injected with the immunogen, preferably using a conventional adjuvant such as Freund's Complete adjuvant or Incomplete adjuvant or the like. Suitable host animals for this purpose include mammals such as rabbits, horses, goats, guinea pigs, rats, cows, sheep, etc. The resulting antisera will contain antibodies, called anti-cannabinoid antibodies, which will selectively complex with tetrahydro-cannabinol metabolites. The suitability of the antiserum (i.e., the anti-cannabinoid antibodies) for use in an immunoassay can be rapidly ascertained by routine experimentation.

In a preferred embodiment according to the present invention, each host is immunized sequentially with three different immuno- gens, each representing a different "metabolite" of THC. Significantly, by immunizing the animals sequentially with three selected different immunogens (e.g., compounds of formula VIII, IX and Xa below)

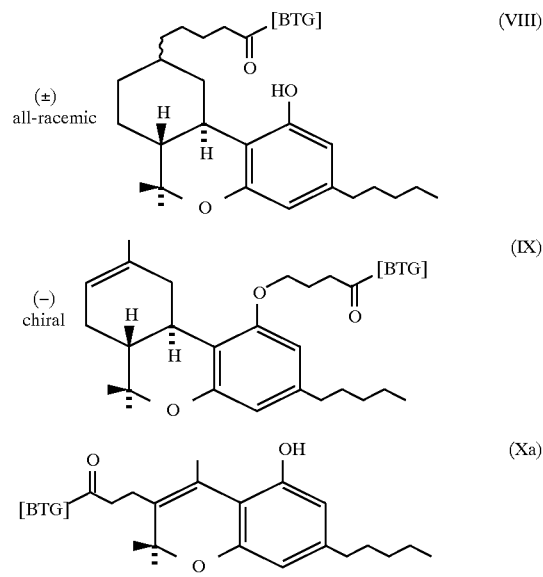

so that no animal's immune system is exposed to a position 1, or a position 9 cannabinoid, or a benzpyran-like derivative more than once in each cycle, one is able to focus the animal's immune response to the non-metabolized benzpyran-like region that is common to all the major metabolites of THC. This sequential immunization strategy leads to hybridoma fusions that are highly successful in producing monoclonal antibodies of high cross-reactivity. This strategy is demonstrated in Example 17 infra.

Analogously, polyclonal antibodies may also be elicited successfully with immunogens containing compounds of formula I. The generation of polyclonal antibodies using selected immunogens is well known. See, e.g., Chase, M. W. The Production of Antiserum, Methods in Immunology and Immunochemistry, Vol. 1 197–209 (1967).

By using the novel immunogens described herein containing novel compounds of Formula I, we have consistently produced antibodies having a higher degree of cross-reactivity to the major THC metabolites than reported previously. We have shown that the inclusion of a novel "truncated cannabinoid" immunogen containing a benzpyran core compound of Formula I, e.g., the benzpyran-containing immunogens Xa and XIIa, acts to direct the specificity of the resulting antibodies towards the core benzpyran portion of the cannabinoids thereby ensuring that these antibodies have broad cross-reactivities to all the major THC metabolites.

The antibodies according to the present invention have an average cross-reactivity to all six major THC metabolites (that is metabolites II, III, IV, V, VI and VII), combined (as opposed to each individual metabolite), of at least about 80%, as measured in an ELISA assay in which, by definition, the cross-reactivity of metabolite II is assigned a value of 100%.

In one preferred embodiment of the present invention, the antibody has the following cross-reactivities, relative to metabolite II which is defined to have 100% cross-reactivity to the antibody, to each of the given THC metabolites:

| Metabolite | % CR |
| --- | --- |
| III | at least about 85% |
| IV | at least about 100% |
| V | at least about 98% |
| VI | at least about 91% |
| VII | at least about 98% |

The fact that antibodies obtained by the procedures taught herein have high cross reactivities to the major THC metabolites when assayed by ELISA (enzyme linked immunosorbant assay) microtiter plates, is demonstrated in Table 1 below.

In Table 1, "% CR" is a measure of the ability of one cross-reactant (i.e., drug), relative to another crossreactant, to displace antibody bound to a 96-well microtiter plate. % CR was calculated as shown in Example 17d. "% D" is a direct measure of the ability of the drug to displace antibody from binding to a microtiter well.

As is shown in Table 1 below, antibodies raised with the two novel benzpyran immunogens Xa and XIIa either alone (Section 1 of the Table, method A) or in conjunction with other immunogens (Section 3 of the Table, method B), consistently exhibit better % CR and % D values than the antibodies raised with either one "intact cannabinoidal" immunogen (e.g., immunogen XIII, Section 2 of the Table) or antibodies raised with two "intact cannabinoidal" immunogens (IX and VIII, Section 4 of the Table).

At the bottom of Table 1 (Section 5) are included the best sets of results when a single immunogen (VIII) is used to immunize mice. As stated above, the resulting cross-reactivities demonstrated by the anti-cannabinoid monoclonal antibodies elicited using method A, multiple boosts with one immunogen, are inferior to those demonstrated by the clones shown in Table 1 that were derived from the multiple immunogen mediated epitope selection method described herein using a novel benzpyran immunogen (method B).

In screening antibody pools, the cross-reactivity to the major THC metabolite (compound of Formula II) was the primary selection criterion.

Use of only the two "intact tricyclic cannabinoidal" immunogens (IX) and (VIII) in a sequential immunization scheme did not generate monoclonal antibodies to cannabinoids having the desired array of cross-reactivities to the various metabolites. The two best clones are shown in Table 1, Section 4 (clones 17-4F12 and 17-5G12). These two clones demonstrate good cross-reactivity to the major metabolite (II), but only moderate to poor cross-reactivities to the other metabolites. See Table 1, Section 4.

Additionally, it is noted that use of either of the benzpyran immunogens (Xa) or (XIIa) alone in a standard multiple-boost immunization program gave polyclonal antisera that showed very good cross-reactivities to all the major metabolites of THC. See Table 1, Section 1. These results confirm that recognition of compounds (i.e., metabolites II through VII) that carry a benzpyran "core" is indeed being induced in the novel antibodies being produced according to the present invention using the disclosed novel immunogens.

TABLE 1

ELISA Cross-Reactivities of Benzpyran Immunogen Induced Antisera/Antibodies and comparison with specified antibodies

| | | | | % Displacement (D) and % Cross-reactivity* (CR) to: | | | | | | | | | | |
| --- | --- | --- | --- | --- | --- | --- | --- | --- | --- | --- | --- | --- | --- | --- |
| | | | | (II) | | (III) | | (IV) | | (V) | | (VI) | | (VII) |
| Immunogen | Method | Antibody I.D. | Species | D | CR | D | CR | D | CR | D | CR | D | CR | D | CR |
| 1. (Xa) | A | 16350-153-257 | Goat Polyclonal | 66 | 100 | 87 | 131 | 80 | 121 | 77 | 116 | 90 | 136 | 87 | 131 |
| (Xa) | A | 16350-153-1172 | Sheep Polyclonal | 55 | 100 | 62 | 112 | 60 | 109 | 53 | 96 | 69 | 125 | 63 | 114 |
| (XIIa) | A | 20903-92-120 | Goat Polyclonal | 52 | 100 | 80 | 153 | 66 | 126 | 68 | 130 | 81 | 155 | 79 | 151 |
| (XIIa) | A | 20903-92-1212 | Sheep Polyclonal | 54 | 100 | 77 | 142 | 73 | 135 | 70 | 129 | 85 | 157 | 73 | 135 |
| 2. (XIII) | A | THC 421 | Goat Polyclonal | 81 | 100 | 25 | 30 | 33 | 40 | 26 | 32 | 31 | 38 | 36 | 44 |
| 3. 1. (IX) 2. (VIII) 3. (Xa) | B | THC 21 11A6.1 | Murine Monoclonal | 94 | 100 | 80 | 85 | 94 | 100 | 93 | 98 | 86 | 91 | 92 | 98 |
| 1. (IX) | B | THC 21-25D3 | Murine | 91 | 100 | 90 | 99 | 91 | 100 | 91 | 100 | 94 | 103 | 92 | 101 |

TABLE 1-continued

ELISA Cross-Reactivities of Benzpyran Immunogen
Induced Antisera/Antibodies and comparison with
specified antibodies

| | | | | % Displacement (D) and % Cross-reactivity* (CR) to: | | | | | | | | | | |
|---|---|---|---|---|---|---|---|---|---|---|---|---|---|---|
| | | | | (II) | | (III) | | (IV) | | (V) | | (VI) | | (VII) | |
| Immunogen | Method | Antibody I.D. | Species | D | CR | D | CR | D | CR | D | CR | D | CR | D | CR |
| 2. (VIII) 3. (Xa) | | | Monoclonal | | | | | | | | | | | | |
| 4. 1. (IX) 2. (VIII) | B | THC 17 4F12 | Murine Monoclonal | 91 | 100 | 7 | 4.4 | 44 | 36 | 22 | 28 | 80 | 89 | 0 | 0 |
| 1. (IX) 2. (VIII) | B | THC 17 5G12 | Murine Monoclonal | 93 | 100 | 32 | 34 | 53 | 54 | 50 | 53 | 86 | 91 | 25 | 26 |
| 5. (VIII) | A | THC 13 1-11E.2 | Murine Monoclonal | 80 | 100 | 23 | 28 | 67 | 8.5 | 23 | 28 | 29 | 36 | 33 | 44 |

*By definition, cross-reactivity of (II) is assigned as 100% and the cross-reactivities of the other compounds are obtained by comparison against (II).
Method A: Multiple Boosts.
Method B: SEQUENTIAL IMMUNIZATION in the order shown.
(II) = $\Delta^9$-9-carboxy-THC
(III) = 8β-OH-$\Delta^9$-THC
(IV) = 11-OH-$\Delta^8$-THC
(V) = 11-OH-$\Delta^9$-THC
(VI) = 8α-OH-$\Delta^9$-THC
(VII) = 8β,11-di-OH-$\Delta^9$-TH The anti-cannabinoid antibodies created according to the present invention can be used in a variety of immunoassays for the detection of tetrahydrocannabinol metabolites. Such immunoassays could take the form of a radioimmunoassay, either in free solution or solid phase. Alternatively, enzyme immunoassays could be carried out, again either in free solution or solid phase. Solid phase assays can be carried out by the use of a solid support, such as a membrane or particles onto which either the antibodies or a cannabinoid label have been immobilized. Particles which may be so coated include, e.g., latex beads, liposomes, erythrocytes, polyacrylamide beads, polystyrene beads or beads made of any of a number of other suitable polymers. The immunoassays can be direct or indirect, with the application of a second antibody directed against the anti-cannabinoid antibodies.

Immunoassays for THC are commonly based on competitive binding between labeled drug and unlabeled drug and metabolites from a clinical sample for a limiting amount of antibody. Free drug or metabolite from a clinical sample will inhibit the binding of the labeled drug to the antibody. The extent to which the clinical sample can inhibit the binding of the labeled drug to the antibody is a direct measurement of the amount of drug present in the clinical sample.

In a preferred embodiment of the present invention, a sample suspected of containing THC or its metabolites is mixed with known amounts of a cannabinoid compound that is bound onto latex microparticles, in the presence of antibody. The degree to which latex will be cross-linked by the antibody is inversely proportional to the amount of drug or metabolite present in the clinical sample. The more drug or metabolite present the less cross-linking that occurs. A specimen can be quantitatively identified as positive by comparison to a standard curve.

Table 2 below illustrates how a novel clone (11A6) derived by using the triple sequential immunization procedure described herein performs in an actual commercial MIRA (Roche Diagnostic Systems, Inc., Branchburg, N.J.) assay ABUSCREEN® 100 TEST ONLINE™ KIT (Roche Diagnostic Systems, Inc., Branchburg, N.J. immunoassay) for cannabinoids. Example 20 describes the reagents contained in Roche's commercial Abuscreen® 100 Test Online™ Kit, except that the antibody has been replaced by a novel antibody according to this invention. The resulting "actual" cross reactivities to several major THC metabolites in the assay using Roche Diagnostic Systems' current labeled microparticles are as shown in Table 2, while the readings for clinical samples (all of which were positive for $\Delta^9$-THC acid by GC/MS) are shown in Table 3. Both tables also report the corresponding results using the monoclonal antibody (11E.2) derived from immunization with a single immunogen (immunogen (VIII)).

In Table 2, MoAb 11E.2 is an IgA (dimeric) antibody, while MoAB 11A6 is an IgG (monomeric) antibody. In order to agglutinate the microparticles included in the current commercial MIRA assay when 11A6 is used, inclusion of an anti-IgG antibody (commercially available, e.g., from Biodesign Int., Kennebunk, Me. 04043, USA) was required.

The data in Table 2 shows that the cross-reactivities of the new MoAb 11A6, in an actual commercial assay, to several major THC metabolites is appreciably higher than those shown by the present commercial MoAb 11E.2. Analogously, the clinical results in Table 3 show that when MoAb 11A6 is used, the relative concentration of cannabinoids to be detected in the samples is higher in all but one case, where it was essentially the same. The average value (that is, "sensitivity" of the assay) was also higher when MoAb 11A6 was used. These higher values are important because it means that the new antibody increases the "pick up rate" for positive samples (i.e., accurately detects a greater number of positive samples) in the assay for cannabinoids.

The antibodies and novel compounds disclosed herein may be conveniently packaged, alone or with other reagents, in the same or different containers in a kit. By way of example, the kit may include an antibody according to this invention; a labeled THC reagent or a labeled THC metabolite reagent; and a set of calibrators that contain a known amount of $\Delta^9$-THC acid.

TABLE 2

| CROSS REACTANT | CROSS REACTIVITY (%) | |
|---|---|---|
| | MoAb 11E.2§ | MoAb 11A6¶ with anti-IgG |
| (−)-$\Delta^9$-11-nor-9-COOH-THC (II) | 100* | 100* |
| (−)-8β,11-Dihydroxy-$\Delta^9$-THC (VII) | 14 | 36 |
| (−)-11-Hydroxy-$\Delta^9$-THC (V) | 23 | 32 |
| (−)-8α-Hydroxy-$\Delta^9$-THC (VI) | 60 | 71 |
| 11-Hydroxycannabinol | 16 | 35 |
| (−)-$\Delta^9$-THC | 7.6 | 7.3 |
| Cannabinol | 0.6 | 1.6 |
| Cannabidiol | <0.1 | <0.1 |

*By definition
§From immunization with (VIII) alone. This is an IgA.
¶From the "triple sequential immunization" with (VIII), (IX), and (Xa). This is an IgG.

TABLE 3

| | Experimental Value of "Cannabinoids" Present in Clinical Sample (ng/mL) | | | GC/MS |
|---|---|---|---|---|
| SAMPLE # | MoAb 11E.2§ | MoAb 11A6¶ with anti IgG | MoAb 11A6¶ with anti-IgG | value@ (ng/mL) |
| 3255 | 40 | 82 | 73 | 33 |
| 3257 | 24 | 49 | 43 | 37 |
| 3258 | 55 | 95 | 92 | 86 |
| 3260 | 49 | 90 | 87 | 82 |
| 3261 | 93 | 100 | 98 | 68 |
| 3262 | 63 | 100 | 89 | 59 |
| 3265 | 50 | 100 | 100 | 73 |
| 3267 | 27 | 69 | 49 | 57 |
| 3272 | 95 | 100 | 94 | 101 |
| 3278 | 44 | 79 | 63 | 42 |
| 3279 | 34 | — | 50 | 44 |
| 3283 | 30 | 50 | 48 | 45 |
| 3285 | 34 | 60 | 51 | 42 |
| 3286 | 34 | 47 | 44 | 84 |
| 3292 | 62 | 96 | 88 | 34 |
| 3293 | 65 | 100 | 100 | 89 |
| 3294 | 85 | 100 | 98 | 73 |
| 3296 | 71 | 100 | 90 | 60 |
| 3297 | 72 | 96 | 88 | 53 |
| 3308 | 69 | 99 | 84 | 63 |
| 3315 | 87 | 100 | 100 | 36 |
| 3316 | 95 | 100 | 99 | 53 |
| 3317 | 77 | 100 | 90 | 53 |
| 3318 | 57 | 100 | 86 | 33 |
| 3321 | 55 | 100 | 97 | 49 |
| Avg. value ("sensivity') | 58.68 | 88.0 | 80.04 | |

§From immunization with (VIII) alone. This is an IgA.
¶From the "triple sequential immunization" with (VIII), (IX), and (Xa). This is an IgG.
@Value for the major metabolite (the standard) $\Delta^9$-11-nor-9-carboxy-THC (II).

EXAMPLES

The following are non-limiting examples which illustrate the synthesis of several novel benzpyran derivatives according to the present invention, the use of these compounds in generating new immunogens, and the use of these immunogens in generating novel antibodies useful in THC detection assays.

General Experimental:

For the following examples, Anhy. tetrahydrofuran (THF) and diethyl ether (Et$_2$O) were obtained by distillation from sodium-benzophenone ketal under argon.

Anhy. methylene chloride (CH$_2$Cl$_2$) was obtained by distillation from calcium hydride under argon.

Preparative layer chromatography (PLC) silica gel plates, thin layer chromatography (TLC) silica gel plates, and flash-grade silica gel were obtained from EM Science.

Example 1

Synthesis of 5-Hydroxy-3-(3-hydroxypropyl)-4-methyl-7-pentyl-2H-1-benzopyran-2-one.

A solution of 30 g (94.2 mmol) of 5-hydroxy-4-methyl-2-oxo-7-pentyl-2H-1-benzopyran-3-propanoic acid (Fahrenholtz, Lurie, and Kierstead; *J. Amer. Chem. Soc.*, 1967, 89, 5934–5941) dissolved in 600 mL of anhy. THF was cooled in an ice-salt bath to −10° C. under argon. To the stirred solution 210 mL (2.2 eq.) of a 1M solution of BH$_3$.THF (Aldrich) was added dropwise, maintaining the reaction temperature at about −6° C. When the addition was complete the reaction was stirred with cooling for 4 hrs and then quenched with 900 mL of ice-cold 2N aq. HCl maintaining the temperature at less than 0° C. The resulting mixture was extracted with EtOAc and the organic phase washed twice with half-saturated aq. brine, followed by sat. aq. brine, dried over sodium sulfate, filtered and evaporated under reduced pressure. The solid obtained was triturated with Et$_2$O and filtered to give 18.8 g, 65%, of 5-Hydroxy-3-(3-hydroxypropyl)-4-methyl-7-pentyl-2H-1-benzopyran-2-one as an off-white solid. HR EI MS: Calc M$^+$, 304.1675; Observed, 304.1675.

Example 2

Synthesis of 5-Hydroxy-2,2,4-trimethyl-7-pentyl-2H-1-benzopyran-3-propanol i) To a solution of 200 mg (0.66 mmol) of 5-Hydroxy-3-(3-hydroxypropyl)-4-methyl-7-pentyl-2H-1-benzopyran-2-one in 20 mL of anhy. THF at reflux under argon was added 1.0 mL (~4.5 eq.) of a 3M solution of methyl magnesium bromide (MeMgBr) (Aldrich) in Et$_2$O that had been diluted to 20 mL with anhy. Et$_2$O dropwise over about 20 min. and the reaction boiled under reflux. A further 2 mL of a 3M solution of MeMgBr (Aldrich) diluted with 8 mL of anhy. Et$_2$O and 10 mL of anhy. THF was added dropwise and the reaction boiled under reflux and under argon for 2 hr. Heat was removed, the reaction cooled to RT, quenched with excess cold 1N HCl and the mixture extracted with EtOAc. The organic phase was evaporated under reduced pressure and the residue subjected to PLC, eluting with 50% EtOAc-hexane, to give 85 mg (42.5%) of recovered starting material, and 42 mg (15%) of the desired product from the less polar product band. This material was resubjected to PLC eluting with 1:1 CHCl$_3$-EtOAc to give 32 mg of clean 5-Hydroxy-2,2,4-trimethyl-7-pentyl-2H-1-benzopyran-3-propanol HR EI MS: Calc M$_+$, 318.2195; Observed, 318.2191.

ii) Alternate Synthesis A solution of 15 mL of a 1M solution of MeMgBr (Aldrich) diluted with 60 mL of anhy. Et$_2$O and 15 mL of anhy. THF was brought to a boil under reflux and under argon. A solution of 1.0 g of 5-Hydroxy-3-(3-hydroxypropyl)-4-methyl-7-pentyl- 2H-1-benzopyran-2-one in 60 mL of dry THF was then added dropwise over 1 hr to the reaction and boiling continued for a total of 4 hr. The reaction was allowed to cool to RT overnight, brought back to a boil and boiling resumed for a further 2 hr. Heating was then stopped and the reaction cooled to RT, then in an ice-bath, and quenched by careful addition of 120 mL of ice-cold 1N HCl with vigorous stirring. The reaction turned yellow, then purplish in color with considerable precipitation of solids, before turning yellow again with clearing of the solution. 40 mL of ice-cold 6N HCl was then added and the mixture stirred in the ice-bath for 15 min. Cooling was then removed, the mixture allowed to attain RT with continuous stirring and the resulting deep yellow solution extracted with EtOAc (1×200 mL, 1×100 mL). The combined organic layers were washed with half-sat. aq. NaCl (3×100 mL), sat. aq. NaCl (1×100 mL), dried ($Na_2SO_4$) and evaporated under reduced pressure to give a discolored syrup. The residue was swirled with about 20 mL EtOAc to give a clear pale colored solution containing off-white solids. The mixture was filtered to give 274 mg of recovered starting material, and a filtrate which was stripped of solvent under reduced pressure to give 760 mg of a material containing product. The material was again triturated with a little EtOAc and filtered again to give a further 159 mg of recovered starting material as a solid, and a filtrate which was stripped of solvent to give 600 mg of a residue which was subjected to PLC, eluting with 1:1 $CHCl_3$-EtOAc. The product band approximately halfway up the plate was isolated, the silica washed with 10% MeOH-EtOAc and the washings evaporated under reduced pressure to give 243 mg of the desired product 5-Hydroxy-2,2,4-trimethyl-7-pentyl-2H-1-benzopyran-3 -propanol.

Example 3

Preparation of 5-(Methoxymethoxy)-2,2,4-trimethyl-7-pentyl-2H-1-benzopyran-3-propanol.

To a solution of 1.96 g (6.16 mmol) of 5-Hydroxy-2,2, 4-trimethyl-7-pentyl-2H-1-benzopyran-3-propanol in 10 mL of anhy. DMF (Aldrich) under argon at RT was added 260 mg (~1.05 eq.) of a 60% dispersion of sodium hydride (Aldrich) and the mixture stirred at RT under argon until effervescence had ceased and the solution had become a clear, darker colored solution. To the stirred solution was added 0.55 mL (~1 eq.) of methoxymethyl chloride (Aldrich, 85% purity technical grade) by syringe directly into the solution with the needle tip below the surface of the solution. The color of the reaction mixture discharged and a precipitate formed within 1 min. Stirring was continued for 0.5 hr. Half of the solution was then withdrawn by syringe for use in another reaction. The remaining half was poured into a mixture of 50 mL of sat. aq. $NaHCO_3$ and 100 mL EtOAc, the mixture shaken well and sufficient water added to dissolve solids that formed to give two clear phases. The phases were separated and the organic phase washed with half-sat. aq. NaCl (2×50 mL), sat. aq. NaCl (1×50 mL), dried ($Na_2SO_4$), evaporated under reduced pressure and the residue dried under high vacuum to give 1.05 g (~94%) of the desired product 5-(Methoxymethoxy)-2,2,4-trimethyl-7-pentyl-2H-1-benzopyran-3-propanol as an oil, shown by $^1$H-NMR to be of good purity.

Material that was recovered from another reaction was further repurified by PLC, eluting with 30% EtOAc-hexane, to give 5-(Methoxymethoxy)-2,2,4-trimethyl-7-pentyl-2H-1-benzopyran-3-propanol which possessed an nmr spectrum that was the same as that of the material isolated as described in the preceding paragraph and which also had: HR EI MS: Calc $M^+$, 362.2457; Observed, 362.2441.

Example 4

Preparation of 5-(Methoxymethoxy)-2,2,4-trimethyl-7-pentyl-2H-1-benzopyran-3-propanoic acid To the half of the final reaction mixture that was withdrawn by syringe in Example 3, containing 5-(Methoxymethoxy)-2,2,4-trimethyl-7-pentyl-2H-1-benzopyran-3-propanol, that was placed in a flask was added a further 20 mL of anhy. DMF (Aldrich). To the stirred solution was added 4.0 g of pyridinium dichromate (Aldrich) in one lot and the dark-colored solution stirred at RT under argon for about 14 hr. The reaction mixture was then diluted with 200 mL of water, stirred, and extracted with EtOAc (1×150 mL, 1×50 mL). The combined organic phases were washed with water (2×50 mL), half-sat. aq. NaCl (2×50 mL), sat. aq. NaCl (1×50 mL), dried ($Na_2SO_4$), evaporated under reduced pressure and the residue dried under high vacuum to give ~0.9 g of a brownish syrup. The material was subjected to column chromatography on flash-grade silica gel, eluting first with $CHCl_3$ and then with 5% MeOH-$CHCl_3$. The fractions containing product were isolated to give from the main cut of the fractions 232 mg of the desired product 5-(Methoxymethoxy)-2,2,4-trimethyl-7-pentyl-2H-1-benzopyran-3-propanoic acid after evaporation of solvent and drying under high vacuum. The fore fractions of the main cut of the product fractions were stripped of solvent and the residue further purified by PLC, eluting with 5% MeOH-$CHCl_3$, to give from the product band a further 32 mg of the desired product 5-(Methoxymethoxy)-2,2,4-trimethyl-7-pentyl-2H-1-benzopyran-3-propanoic acid. HR EI MS: Calc $M^+$, 376.2250; Observed, 376.2246.

Example 5

Preparation of 5-Hydroxy-2,2,4-trimethyl-7-pentyl-2H-1-benzopyran-3-propanoic acid To a solution of 0.55 g (1.65 mmol) of 5-(Methoxymethoxy)-2,2,4-trimethyl-7-pentyl-2H-1-benzopyran-3-propanoic acid in 60 mL of tert-butyl alcohol (MCB Chem. Co.) under argon was added 4.16 g (10 eq.) of pyridinium para-toluenesulfonic acid (Aldrich) and the reaction mixture boiled under reflux for 1 hr. The reaction mixture was cooled with an ice-water bath and then partitioned between 500 mL of EtOAc and 100 mL of water. The phases were separated and the organic phase washed with water (5×100 mL), half-sat. aq. NaCl (1×100 mL), sat. aq. NaCi (1×100 mL), dried ($Na_2SO_4$), evaporated under reduced pressure and the residue dried under high vacuum to give discolored solids. The solids were redissolved and subjected to column chromatography on flash-grade silica gel, eluting with 10% MeOH-$CHCl_3$. The fractions containing product were combined and solvent removed under reduced pressure to give, after drying under high vacuum, 143 mg of 5-Hydroxy-2,2,4-trimethyl-7-pentyl-2H-1-benzopyran-3-propanoic acid as a glass/amorphous solid. HR EI MS: Calc $M^+$, 332.1988; Observed, 332.1985.

Example 6

Preparation of the hapten 1-[3-(5-Hydroxy-2,2,4-trimethyl-7-pentyl-2H-1-benzopyran-3-yl)-1-oxopropoxy]-2,5-pyrrolidinedione (X)

i) To a solution of 6 mg (0.018 mmol) of the acid 5-Hydroxy-2,2,4-trimethyl-7-pentyl-2H-1-benzopyran-3-propanoic acid in anhy. methylene chloride under argon was added 10.3 mg (5 eq.) of N-hydroxysuccinimide (NHS) (Aldrich) followed by 8.6 mg (2.5 eq.) of 1-ethyl-3-(dimethylaminopropyl)carbodiimide hydrochloride (EDC.HCl) (Sigma). After stirring at RT under argon for 4 hr TLC indicated only traces of starting material were left. The reaction mixture was directly subjected to chromatography on silica gel plates, eluting with 50% EtOAc-hexane. The product band was isolated, washed with a little EtOAc, the washings stripped of solvent under reduced pressure and the residue dried under high vacuum to give 5 mg (65%) of 1-[3-(5-Hydroxy-2,2,4-trimethyl-7-pentyl-2H-1-benzopyran-3-yl)-1-oxopropoxy]-2,5-pyrrolidinedione as a foam. HR (+) FAB MS: Calc (M+H), 430.2230; Observed, 430.2266.

ii) Alternate Synthesis To a solution of 100 mg (0.30 mmol) of the acid 5-Hydroxy-2,2,4-trimethyl-7-pentyl-2H-1- benzopyran-3-propanoic acid in 15 mL of anhy. THF under argon and cooled in an ice-water bath was added 150 mg (3 eq) of carbonyldiimidazole (CDI) (Fluka Chem. Co.) as a solid in one lot. The reaction was stirred at ~0° C. for ~1 hr. The ice bath was removed and the stirred reaction allowed to warm up to RT over 1.5 hr. To the reaction was then added 345 mg (10 eq) of N-hydroxysuccinimide (NHS) (Aldrich) as a solid in one lot and the reaction stirred at RT under argon for 18 hrs. The reaction mixture was then evaporated under reduced pressure and the residue partitioned between 100 mL of EtOAc and 30 mL of 0.1N aq. HCl. The phases were separated and the organic layer washed with 0.1N HCl (2×30 mL), water (1×30 mL), 50 mM phosphate buffer pH 8 (3×30 mL), sat. aq. NaCi (1×30 mL), dried ($Na_2SO_4$), evaporated under reduced pressure and the residue dried under high vacuum. The residue was then subjected to PLC, eluting with 50% $EtOAc-CH_2Cl_2$. The upper product band was isolated and the silica washed with EtOAc. The washings were evaporated under reduced pressure and dried under high vacuum to give 44 mg of the desired product 1-[3-(5-Hydroxy-2,2,4-trimethyl-7-pentyl-2H-1-benzopyran-3-yl)-1-oxopropoxy]-2,5-pyrrolidinedione as a glass/amorphous solid.

Example 7
Preparation of 3,4-Dihydro-5-hydroxy-3-(3-hydroxylpropyl)-4-methyl-7-pentyl-2H-1-benzopyran-2-one To a solution of 4.0 g (13.14 mmol) of 5-Hydroxy-3-(3-hydroxypropyl)-4-methyl-7-pentyl-2H-1-benzopyran-2-one in 500 mL of distilled methanol (from magnesium methoxide) under argon 12.8 g (525.6 mmol) of magnesium turnings was added. The mixture was warmed to initiate the reaction. The reaction was then boiled under reflux overnight. The mixture was cooled to about 0° C. in an ice bath and cautiously quenched with 300 mL of ice-cold 6N aq. HCl. The methanol was removed under reduced pressure and the residue extracted with EtOAc. The organic phase was washed with sat. aq. NaCl, dried, and evaporated under reduced pressure. The solid obtained was purified by flash chromatography on silica gel eluting with a gradient of 30% EtOAc-hexane to 50% EtOAc-hexane to give, from the fractions containing product, 3.06 g (76%) of 3,4-Dihydro-5-hydroxy- 3-(3-hydroxypropyl)-4-methyl-7-pentyl-2H-1-benzopyran-2-one, as a solid. HR EI MS: Calc $M^+$, 306.1831; Observed, 306.1829. The cis/trans ratio was 1:2 as shown by $^1$H-NMR.

Example 8
Preparation of 5-Pentyl-2-[1-(tetrahydro-2,2-dimethyl-2H-pyran-3-yl)ethyl]-1,3-benzenediol To a boiling solution of 19.6 mL (5.87 mmol) of methyl magnesium bromide (3M in $Et_2O$; Aldrich) dissolved in 160 mL of anhy. $Et_2O$ under argon was added dropwise a solution of 4.5 g (14.69 mmol) of 3,4-Dihydro-5-hydroxy-3-(3-hydroxypropyl)-4-methyl-7-pentyl-2H-1-benzopyran-2-one and the reaction was maintained at reflux temperature overnight. The reaction was cooled to 0° C. in an ice bath and cautiously quenched with 2N aq. HCl. The mixture was then extracted with EtOAc and the combined organic phases washed with half-sat. aq. NaCl (×2), sat. aq. NaCl (×1), dried and evaporated under reduced pressure to give 4.5 g of 5-Pentyl-2-[1-(tetrahydro-2,2-dimethyl-2H-pyran-3-yl)ethyl]-1,3-benzenediol which was used without further purification in the next step. A sample was purified to give material which had: HR EI MS: Calc $M^+$, 320.2351; Observed, 320.2348.

Example 9
Preparation of rac-3,4-Dihydro-5-hydroxy-2,2,4-trimethyl-7-pentyl-2H-1-benzopyran-3-propanol A solution of 9.4 g of 5-Pentyl-2-[1-(tetrahydro-2,2-dimethyl-2H-pyran-3-yl)ethyl]-1,3-benzenediol in 400 mL of toluene containing a catalytic amount of pyridinium para-toluenesulfonic acid (Aldrich) was heated to 60° C. under argon for 2 hr. The reaction was cooled to RT, diluted with EtOAc, washed with 0.1N aq. HCl (×2), water (×2), sat. aq. $NaHCO_3$, dried and evaporated under reduced pressure. The material obtained was purified by extensive chromatography to give 3.4 g (35%) of rac-3,4-Dihydro-5-hydroxy-2,2,4-trimethyl-7-pentyl-2H-1-benzopyran-3-propanol as a pale yellow amorphous solid. HR EI MS: Calc $M^+$, 320.2351; Observed, 320.2377. Ratio of 3:1 diastereoisomers as shown by $^1$H-NMR.

Example 10
Preparation of 5-[[1,1-Dimethylethyl)diphenylsilyl]oxy]-3.4-dihydro-2,2,4-trimethyl-7-pentyl-2H-1-benzopyran-3-propanol A solution of 3.17 g (8.78 mmol) of rac-3,4-Dihydro-5-hydroxy-2,2,4-trimethyl-7-pentyl-2H-1-benzopyran-3-propanol in 60 mL of anhy. DMF (Aldrich) was added to a suspension of 383 mg (1 eq) of sodium hydride (Aldrich) in 20 mL of anhy. DMF (Aldrich) and the mixture stirred at RT under argon for 0.5 hr. 2.28 mL (1 eq.) of tert-butylchlorodiphenylsilane (Aldrich) was then added by syringe. After stirring for 2 hr at RT the reaction was diluted with EtOAc, washed with 0.1N aq. HCl, water, sat. aq. NaCl, dried and evaporated under reduced pressure. The residue was purified by flash chromatography on silica gel, eluting with 30% EtOAc-hexane. The fractions containing the product were combined and evaporated under reduced pressure to give 2.23 g (45%) of 5-[[(1,1-Dimethylethyl)diphenylsilyl]oxy]-3,4-dihydro-2,2,4-trimethyl-7-pentyl-2H-1-benzopyran-3-propanol as a pale yellow oil. HR EI MS: Calc $M^+$, 558.3530; Observed, 558.3516.

Example 11
Preparation of 5-[[(1 1-Dimethylethyl)diphenylsilyl]oxy]-3,4-dihydro-2,2,4-trimethyl-7-pentyl-2H-1-benzopyran-3-propanoic acid A mixture of 2.2 g (3.97 mmol) of 5-[[(1,1-Dimethylethyl)diphenylsilyl]oxy]-3,4-dihydro-2,2,4-trimethyl-7-pentyl-2H-1-benzopyran-3-propanol and 7.47 g (19.86 mmol) of pyridinium dichromate (Aldrich) in anhy. DMF (Aldrich) was stirred at RT under argon for 20 hr. The reaction was diluted with water and extracted with EtOAc. The organic phase was dried and solvent removed under reduced pressure. The residue was then purified by repeated chromatography on silica gel to give 1.1 g (48%) of 5-[[(1,1-Dimethylethyl)diphenylsilyl]oxy]-3,4-dihydro-2,2,4-trimethyl-7-pentyl-2H-1-benzopyran-3-propanoic acid as a pale yellow foam. HR EI MS: Calc $M^+$, 572.3322; Observed, 572.3315. Ratio of 8:1 diastereoisomers as shown by $^1$H-NMR.

Example 12
Preparation of 3,4-Dihydro-5-hydroxy-2,2,4-trimethyl-7-pentyl-2H-1-benzopyran-3-propanoic acid A solution of 1.0 g (1.75 mmol) of 5-[[(1,1-Dimethylethyl)-diphenylsilyl]oxy]-3,4-dihydro-2,2,4-trimethyl-7-pentyl-2H-1-benzopyran-3-propanoic acid in anhy. THF under argon was treated with 2.09 mL (2.09 mmol) of a 1M solution of tetrabutylammonium fluoride in THF (Aldrich). After stirring at RT for 1 hr the reaction was evaporated under reduced pressure and the residue subjected to column chromatography on flash-grade silica gel, eluting with 5% $MeOH-CHCl_3$. The fractions containing product were combined and evaporated under reduced pressure to give 395 mg (67%) of 3,4-Dihydro-5-hydroxy-2,2,4-trimethyl-7-pentyl-2H-1-benzopyran-3-propanoic acid as a tan-colored foam. MA: Calc for $C_{20}H_{30}O_4 \cdot 0.2H_2O$: C, 71.06; H, 9.06; O, 19.29. Found: C, 70.93; H, 8.95; O, 19.27.

Example 13
Preparation of 1-[3-(3,4-Dihydro-5-hydroxy-2,2,4-trimethyl-7-pentyl-2H-1-benzopyran-3-yl)-1-oxopropoxy]-2,5-pyrrolidinedione, (XII)

To a solution of 297 mg (0.88 mmol) of 3,4-Dihydro-5-hydroxy-2,2,4-trimethyl-7-pentyl-2H-1-benzopyran-3-propanoic acid in 20 mL of anhy. $CH_2Cl_2$ under argon was added 246 mg (2.14 mmol) of N-hydroxysuccinimide (Aldrich) and the reaction stirred for 15 min. 408 mg (2.14 mmol) of 1-ethyl-3-(dimethylaminopropyl)carbodiimide (Sigma) was then added and the reaction stirred at RT for 3 hr. The reaction was diluted to five times the volume with $CH_2Cl_2$, washed with 0.1N aq. HCl that had been saturated with NaCl, followed by sat. aq. NaCl, followed by sat. aq. $NaHCO_3$ (×3), dried and evaporated under reduced pressure. The residue was purified by flash chromatography on silica gel, eluting with 1:1 EtOAc-$CH_2Cl_2$. The product fractions were combined and evaporated under reduced pressure and dried under high vacuum to give 297 mg (78%) of 1-[3-(3,4-Dihydro-5-hydroxy-2,2,4-trimethyl-7-pentyl-2H-1-benzopyran-3-yl)-1-oxopropoxy]-2,5-pyrrolidinedione as a white foam. HR (+) FAB MS: Calc (M+H), 432.2386; Observed, 432.2413.

Example 14
Preparation of 3-(5-Hydroxy-2,2,4-trimethyl-7-pentyl-2H-1-benzopyran-3-yl)-1-oxopropyl-[Bovine Thyroglobulin], (Xa)

To a solution of 478 mg of purified bovine thyroglobulin (BTG) in 10.0 mL of 50 mM potassium phosphate buffer (KPi) pH 7.5 cooled in an ice-bath was slowly added (dropping funnel) with constant stirring 30 mL of dimethyl sulfoxide (DMSO) over about 30–40 min., to give a solution of protein in 75% DMSO-50 mM phosphate buffer. From the resulting solution 3.2 mL of solution was removed and kept as the control sample. To the remaining solution, containing about 440 mg BTG, was added in one lot a solution of 44 mg of 1-[3-(5-Hydroxy-2,2,4-trimethyl-7-pentyl-2H-1-benzopyran-3-yl)-1-oxopropoxy]-2,5-pyrrolidinedione in about 3 mL of DMSO. The reaction was allowed to warm up to RT overnight with stirring. The slightly cloudy reaction solution was transferred to dialysis tubing (SpectraPor 7; molecular weight cut-off 50,000). The BTG control was also transferred to dialysis tubing. Both solutions were dialyzed at RT sequentially against 2 L each of 75% DMSO-50 mM KPi pH 7.5; 50% DMSO-50 mM KPi pH 7.5; 25% DMSO-50 mM KPi pH 7.5; and 50 mM KPi pH 7.5; before dialyzing against 6×4 L of 50 mM KPi pH 7.5 at 4° C. The resulting retentates were separately filtered through 0.8μ filter units. 75 mL of the conjugate (immunogen) Xa was obtained as a solution in 50 mM KPi pH 7.5. The protein concentration was determined (Coomassie Blue) to be 4.6 mg protein/mL, using the BTG control as the standard. The extent of available lysine modification was determined (Trinitrobenzene-sulfonic acid [TNBS] method) to be about 69%, as measured against the BTG control.

Example 15
Preparation of 3-(3,4-Dihydro-5-hydroxy-2,2,4-trimethyl-7-pentyl-2H-1-benzopyran-3-yl)-1-oxopropyl-[Bovine Thyroglobulin], (XIIa)

In a similar manner to the preparation of immunogen (Xa) given in Example 14 above, a solution of 700 mg of purified BTG in 24 mL of 50 mM KPi pH 7.5 was cooled in an ice-bath and diluted slowly with 72 mL of DMSO over about 1.33 hr. to give a solution of the protein in 75% DMSO-50 mM KPi pH 7.5. A BTG control was prepared with a small portion of BTG in a similar manner. A solution of 70 mg of the hapten 1-[3-(3,4-Dihydro-5-hydroxy-2,2,4-trimethyl-7-pentyl-2H-1-benzopyran-3-yl)-1-oxopropoxy]-2,5-pyrrolidinedione in about 3 mL of DMSO was then added in one lot to the 700 mg of protein and the reaction allowed to warm up to RT with stirring overnight. Dialysis of both the conjugate and of the BTG control then followed in a similar manner to that described in Example 14. Filtration of the final conjugate retentate then gave 115 mL of a solution of immunogen (XIIa) in 50 mM KPi pH 7.5. The protein concentration was determined (Coomassie Blue) to be 3.8 mg/mL using the BTG control as the standard. The extent of available lysine modification was determined (TNBS method) to be about 88%, as measured against the BTG control.

Example 16
Preparation of Immunogens (VIII), (IX), and (XIII)
a. Immunogen (VIII); [9R,S-(6aα,10aβ)]-[5-(6a,7,8,9,10,10a-Hexahydro-1-hydroxy-6,6-dimethyl-3-pentyl-6H-dibenzo [b,d]-pyran-9-yl)-1-oxopentyl]-[Bovine Thyroglobulin].

To a solution of 1.10 g of bovine thyroglobulin (BTG) in 22 mL of 50 mM $NaHCO_3$ pH 8.0 and 66 mL of DMSO was added at room temperature 6.8 mL of a solution of 1.00 g of the cannabinoid derivative [9R,S-(6aα,10aβ)]-1-[5-(6a,7,8,9,10,10a-hexahydro-1-hydroxy-6,6-dimethyl-3-pentyl-6H-dibenzo[b,d]pyran-9-yl)-1-oxopentyloxy]-2,5-pyrrolidinedione (see also: U.S. Pat. No. 4,833,073) and having the formula

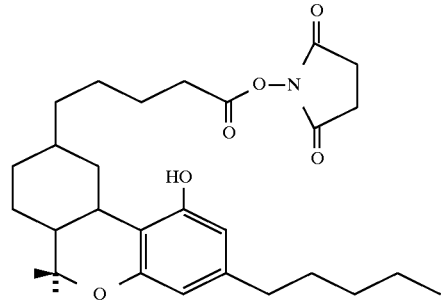

in 14 mL of DMSO. The solution was stirred at room temperature overnight. The resulting solution was transferred to dialysis tubing and dialyzed sequentially against six changes of DMSO-50 mM KPi pH 7.5 with gradually decreasing amounts of DMSO before dialyzing against 5 changes of 50 mM KPi pH 7.5. The BTG control was treated in a similar manner. The retentate from dialysis of the conjugate was then centrifuged to remove a small amount of solid material and the supernatant decanted off to give a solution of the immunogen (VIII) in 50 mM KPi pH 7.5. The protein concentration was determined (Bio-Rad Coomassie Blue protein assay) to be about 4.7 mg/mL. The extent of modification of available lysines was determined (TNBS method) to be about 98%, as measured against a BTG control.

b. Immunogen (IX); (6aR-trans)-4-[(6a,7,10,10a-Tetrahydro-6,6,9-trimethyl-3-pentyl-6H-dibenzo[b,d]pyran-1-yl)oxy]-1-oxobutyl]-[Bovine Thyroglobulin].

To a solution of 700 mg of bovine thyroglobulin in 13.3 mL of 50 mM KPi pH 7.5 and 39.8 mL of DMSO cooled in an ice-water bath was added a solution of 90 mg of the cannabinoid derivative (6aR-trans)-1-[4-[(6a,7,10,10a,-tetrahydro-6,6,9-trimethyl-3-pentyl-6H-dibenzo [b,d]pyran-1-yl)oxy]-1-oxobutoxy]-2,5-pyrrolidinedione having the formula

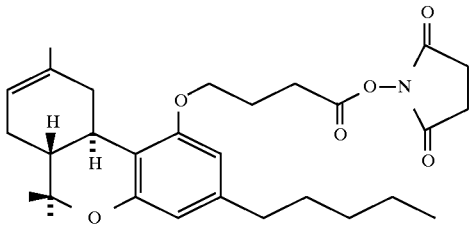

in 2.5 mL of DMSO. The reaction was allowed to warm up to room temperature overnight with stirring. Dialysis of the conjugate was then performed in a similar manner to that described in Example 14. Filtration of the final conjugate retentate then gave 118 mL of a solution of immunogen (IX) in 50 mM KPi pH 7.5. The protein concentration was determined (Coomassie Blue) to be 5.0 mg/mL using a control sample of BTG as the standard. The extent of modification of available lysines on the protein (TNBS method) was determined to be about 95%, as measured against a BTG control.

c. Immunogen (XIII); [9R,S-(6aα, 10aβ)]-[[(6a,7,8,9,10, 10a-Hexahydro-1-hydroxy-6,6-dimethyl-3-pentyl-6H-dibenzo[b,d]-pyran-9-yl)methyl]carbonyl]-[Bovine Thyroglobulin].

To an ice-bath cooled solution of 1.40 g of bovine thyroglobulin (BTG) in 28 mL of 50 mM NaHCO$_3$ pH 8.0 was slowly added 84 mL of DMSO to give a solution of BTG in 75% DMSO-50 mM NaHCO$_3$ pH 8.0 and the solution allowed to warm to room temperature. To the protein solution was added 4.5 mL of a solution of 1073 mg of the cannabinoid derivative [9R,S-(6aα,10aβ)]-1-[2-(6a,7, 8,9,10,10a-hexahydro-1-hydroxy-6,6-dimethyl-3-pentyl-6H-dibenzo[b,d]pyran-9-yl)-1-oxoethyloxy]-2,5-pyrrolidinedione and having the formula

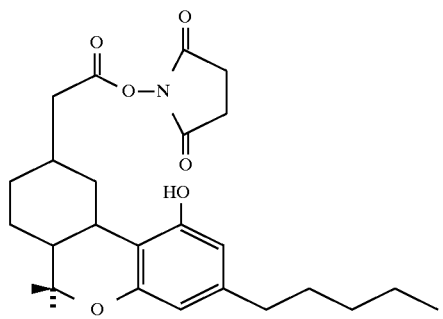

in 16 mL of DMSO and the solution allowed to stir overnight. The resulting solution was transferred to dialysis tubing and dialyzed sequentially against six changes of DMSO-50 mM KPi pH 7.5 with gradually decreasing amounts of DMSO before dialyzing against 5 changes of 50 mM KPi pH 7.5. The retentate from dialysis of the conjugate was then centrifuged to remove a small amount of solid material and the supernatant decanted off to give a solution of the immunogen (XIII) in 50 mM KPi pH 7.5. The protein concentration was determined (Bio-Rad Coomassie Blue protein assay) to be about 3 mg/mL. The extent of modification of available lysines was determined (TNBS method) to be about 98%, as measured against a BTG control.

Example 17
Procedure for Preparation of Monoclonal Antibodies
a. Immunization Procedure:

Eight to 10 week old Balb/C mice (Jackson Laboratories) were injected with a series of three immunogens intraperitoneally in a sequential fashion. First, on day 0, mice were injected with 100 μg of position 9 linked cannabinoid-Bovine Thyroglobulin (BTG) conjugate, immunogen (VIII), emulsified in Complete Freund's Adjuvant (CFA) in a 1:1 ratio. On day 25, mice were boosted with 100 μg of position 1 linked cannabinoid-BTG conjugate, immunogen (IX), emulsified in Incomplete Freund's Adjuvant in a 1:1 ratio. A final boost series was administered using the benzpyran-BTG immunogen (Xa) using 400 μg, 200 μg, and 200 μg diluted in PBS and given at 72 hrs, 48 hrs, and 24 hrs, respectively, prior to cell fusion.

b. Fusion Procedure:

Splenocytes from an immunized mouse were isolated and fused to NSO myeloma cells in a 4:1 ratio using 50% polyethylene glycol as per the procedures of Fazekas de Groth and Scheidegger (F. de St. Groth and D. Scheidegger *J. Immunological Methods*, 35:1–21, 1980.) and G. Kohler and C. Milstein *Nature* (London), 256, pp495–97 (1975)). NSO Cells were plated at 250,000 cells/mL in 96-well microtiter plates and incubated at 37° C. in a 9% CO$_2$ incubator until the clones were of sufficient size to screen.

c. Elisa Analysis of Hybridomas:

Ninety-six well microtiter plates were coated with 50 μL of 5 μg/mL cannabinoid-Bovine Serum Albumin (BSA) Conjugate (XIV), diluted in PBS and incubated for 2 hrs at room temperature. The liquid was removed from the plates by flicking them into a sink and blotting the plates onto absorbant paper. One hundred microliters of 1% BSA in {PBS/azide} was dispensed into each well and the plates are incubated for 1 hr at room temperature. Following the incubation, the plates were washed 3× with {PBS/0.01% Tween 20}. Twenty-five microliters of 1% BSA was added to the wells of each plate, followed by 25 μL of cell supernatant from each of the wells of the cell fusion. The plates were covered and incubated at 37° C. for 1 hr. The plates were washed on the plate washer 3 times with {PBS/Tween 20} and 50 μL of anti-mouse antibody conjugated to alkaline phosphatase were added to each well. The plates were incubated at 37° C. for one hour and were then washed as described above. The assay was developed by the addition of 1 mg/mL para-nitrophenol phosphate dissolved in diethanolamine buffer at pH 9.8. The substrate-containing plates were incubated at room temperature for 30 minutes. Fifty μL of 3M NaOH were added to the wells to stop the enzyme reaction. The plates were read immediately at 405 nm.

d. Competition Assay and Analysis of Crossreactivity:

The competition assays were set-up as above except that free drug was added to the plate in the presence of antibody containing cell supernatants. The crossreactivity was calculated using the equation provided below. All calculations were based upon binding and displacement at the 50% of maximum O.D. (optical density) binding point.

$$\% CR = \frac{(O.D \text{ without crossreactant (i.e., drug)} - O.D \text{ with crossreactant drug})}{(O.D \text{ without }^9\text{-THC acid} - O.D \text{ with } D^9 - \text{THC acid})} \times (100/C.F)$$

Wherein: C.F. is a correction factor used to account for the different levels of crossreactant that may be used in an assay. C.F.=ng of crossreactant/ng Δ$^9$-THC acid. The term "drug" is defined as any crossreactant applied to the assay system.

e. Ascites Generation:

Eight to ten week old Balb/C female mice were primed with 0.5 mL pristane 7–14 days prior to injection of the cells for ascites.

Ascites fluid was recovered as per methods well known in the art. See. e.g., N. Hoogenraad, T. Helman, and J. Hoogenraad, J. *Immunological Methods*, 61, pp317–320 (1983)).

Example 18

Cannabinoid-BSA conjugate (XIV); [9R,S-(6aα,10aβ)]-[5-(6a,7,8,9,10,10a-Hexahydro-1-hydroxy-6,6-dimethyl-3-pentyl-6H-dibenzo[b,d]pyran-9-yl)-1-oxopentyl]-[Bovine Serum Albumin].

To a solution of 250 mg of Bovine Serum Albumin (BSA) in 5 mL of [50 mM KPi pH 7.5] and 14 mL of DMSO cooled in an ice-water bath was added a solution of 3.6 mg of [9R,S-(6aα,10aβ)]-1-[5-(6a,7,8,9,10,10a-hexahydro-1-hydroxy-6,6-dimethyl-3-pentyl-6H-dibenzo[b,d]pyran-9-yl)-1-oxopentyloxy]-2,5-pyrrolidinedione having the formula

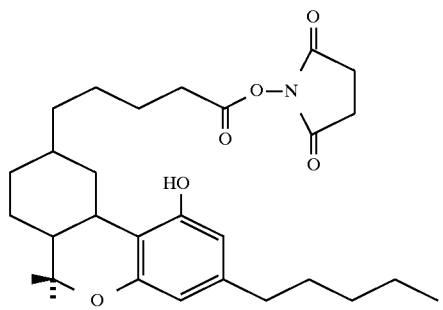

in 1 mL of DMSO. See also U.S. Pat. No. 4,833,073. The solution was stirred overnight at room temperature and then transferred to dialysis tubing (with a molecular weight cut-off of 10,000) and dialyzed in a similar manner to that described in Example 14. Filtration of the final conjugate retentate then gave 45 mL of a solution of conjugate (XIV) in 50 mM KPi pH 7.5. The protein concentration was determined (Coomassie Blue protein assay) to be 4.9 mg/mL as measured against a standard sample of BSA.

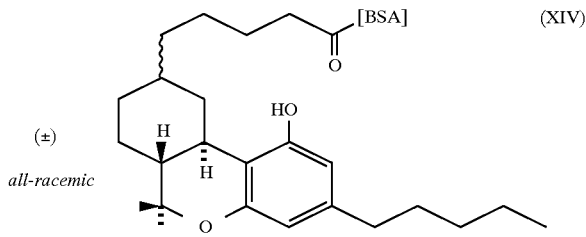

Example 19

Procedure for Preparation of Polyclonal Antisera

Six month to one year old goats and sheep were immunized with 3 mg of immunogen conjugate on day 0 emulsified in Complete Freunds Adjuvant. Subsequent immunizations were with 1–3 mg of immunogen conjugate emulsified in Incomplete Freund's Adjuvant given every four weeks. Blood was then taken from the animals and antisera prepared according to methods known in the art. See, e.g. E. Harlow and D. Lane, Antibodies: A Laboratory Manual, Cold Spring Harbor, 1988, pp 92–114).

The immunogens used were those identified in Table 1. The plate coating was the cannabinoid—Bovine Serum Albumin (BSA) conjugate (XIV).

Example 20

This example describes the reagents contained in Roche's ABUSCREEN® 100 TEST ONLINE™ KIT (Roche Diagnostic Systems, Inc., Branchburg, N.J. immunoassay) for cannabinoids.

Assay Reagents

1. Antibody Reagent: A cannabinoid monoclonal antibody (IgG) with a secondary antibody adjusted in concentration to give the best dynamic standard curve with desired performance characteristics around the assay cutoff. This antibody is diluted in an antibody diluent containing: 50 mM HEPES, 0.1% BSA, 0.5% sodium chloride, 0.09% sodium azide and adjusted to a pH of 6.5.

2. Microparticle Reagent: Conjugated cannabinoids derivative microparticle in a buffer containing 10 mM kPi pH 7.5 and 0.09% sodium Azide (supplied in kit).

3. Sample Diluent: Buffer containing 50 mM PIPES pH 7.0, 2.5% PVP, 2.0% Sodium Chloride and 0.09% sodium azide (supplied in kit).

Additional Reagents

Abuscreen® Online™ cannabinoids calibration pack.

An assay using the above reagents is performed pursuant to the directions stated in the package insert for the commercially available Roche Abuscreen® Online™ 100 test kit for cannabinoids.

We claim:

1. An immunogen derived a from compound having the formula

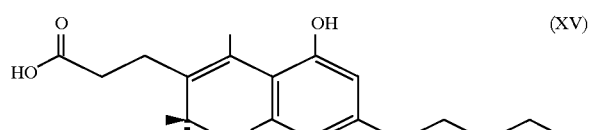

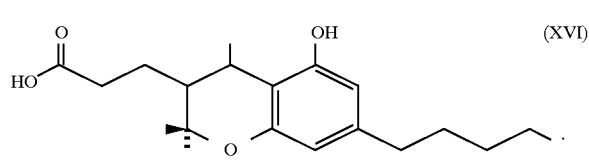

2. An immunogen derived from a compound having the formula

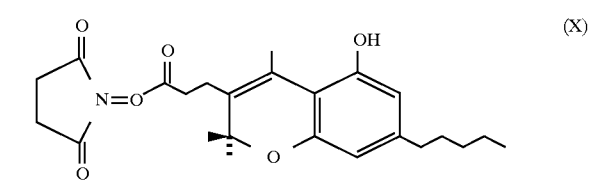

or

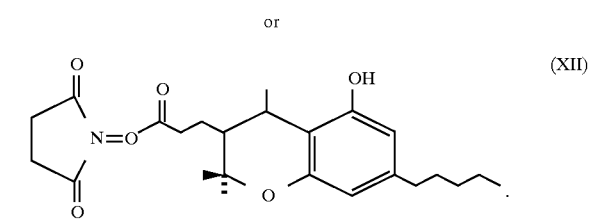

3. An immunogen derived from at least one compound of formula

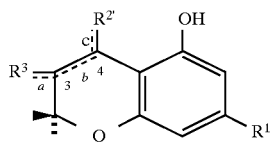
(I)

wherein $R^1$ is a linear or branched alkyl group having from 1 to 9 carbon atoms; $R^2$ and $R^3$ are independently selected from linear or branched lower alkyl which can be substituted by one or more of the following functional groups —OH, —COR$^4$, —NR$^5$R$^6$, —SH, —C(=NH)—OR$^7$, —CHO, or =O, provided that at least one of $R^2$ or $R^3$ is substituted by at least one of the above-described functional groups; $R^4$ is —OH or is a leaving group; $R^5$ and $R^6$ are independently selected from the group consisting of H and linear or branched lower alkyl; $R^7$ is linear or branched lower alkyl; and a, b, and c are independently single or double bonds, provided that when b is a double bond, then a and c are not double bonds.

4. The immunogen of claim 7 comprising a proteinatious carrier.

5. The immunogen of claim 4 wherein the proteinatious carrier is selected from the group consisting of a thyroglobulin, a serum albumin, a globulin, and a haemocyanin.

6. The immunogen of claim 5 wherein the proteinatious carrier is selected from BTG or BSA.

7. The immunogen of claim 4 further comprising a chemical linker between the compound of formula I and the proteinatious carrier.

8. An immunogen selected from

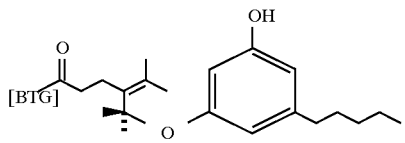
(Xa)

and

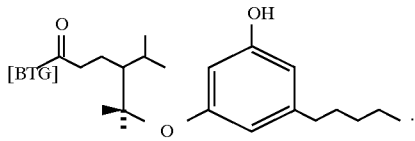
(XIIa)

wherein BTG is bovine thyroglobulin.

9. An antibody that has an average cross-reactivity, combined, of at least about 80%, as measured by displacement in an ELISA assay, to all of the following THC metabolites:

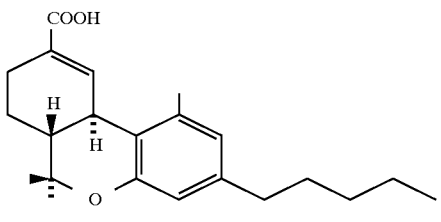
$\Delta^9$-THC acid (II)

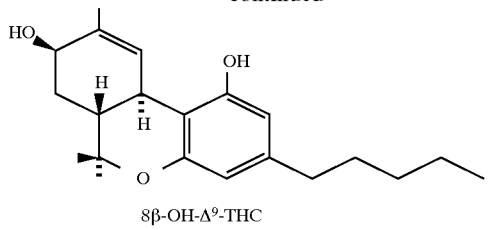
8β-OH-$\Delta^9$-THC (III)

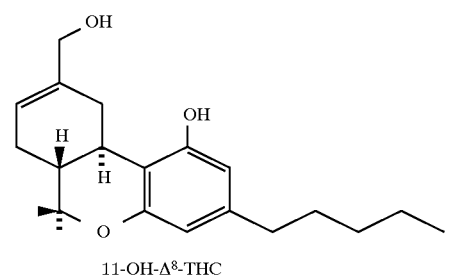
11-OH-$\Delta^8$-THC (IV)

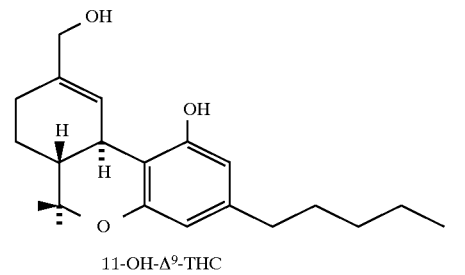
11-OH-$\Delta^9$-THC (V)

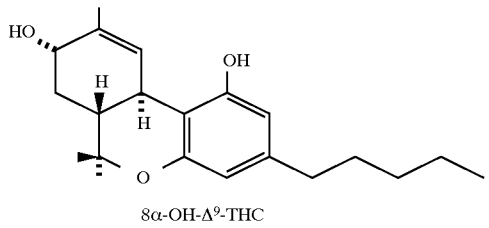
8α-OH-$\Delta^9$-THC (VI)

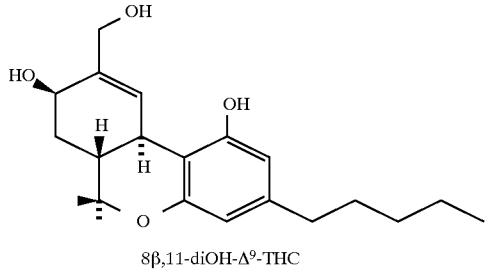
8β,11-diOH-$\Delta^9$-THC (VII)

10. The antibody of claim 9 that is a monoclonal antibody.

11. The antibody of claim 10 that has the following cross-reactivities, relative to metabolite II, to the following THC metabolites:

| Metabolite | % CR |
|---|---|
| III | at least about 85%; |
| IV | at least about 100%; |
| V | at least about 98%; |
| VI | at least about 91%; and |
| VII | at least about 98%. |

12. The antibody of claim 9 that is polyclonal.

13. A method of preparing monoclonal antibodies to cannabinoids, the improvement comprising immunizing the host with at least one immunogen in accordance with claim 3.

14. A method of preparing monoclonal antibodies to cannabinoids, the improvement comprising immunizing the host sequentially with the following immunogens:

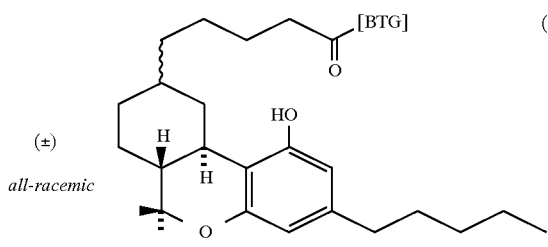

(VIII)

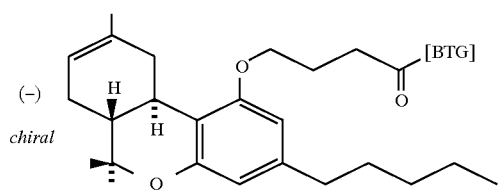

I(X)

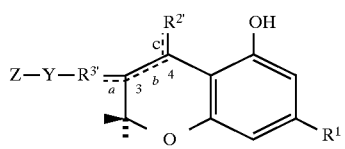

(Ia)

wherein R¹ is a linear or branched alkyl group having from 1 to 9 carbon atoms; R²' is linear or branched lower alkyl; R³' is linear or branched lower alkyl which is substituted by —O—, —CO—, —NR⁵—, —NR⁶—, —S—, —C(=NH)—, —CH=, —CH₂—; R⁵ and R⁶ are independently selected from the group consisting of H, and linear or branched lower alkyl; Y is a linking group or a bond; Z is a carrier; and a, b, and c are independently single or double bonds, provided that when b is a double bond. then a and c are not double bonds.

15. The method of claim 14 wherein immunogen (Ia) is

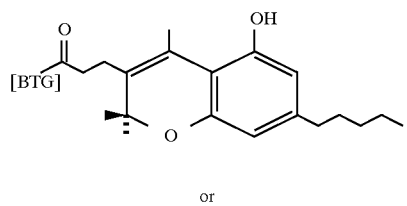

(Xa)

or

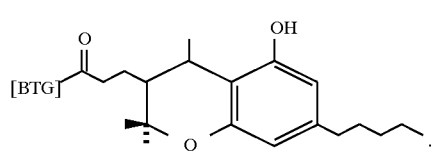

(XIIa)

16. A method for preparing monoclonal antibodies to cannabinoids, the improvement comprising immunizing the host with at least one compound of formula

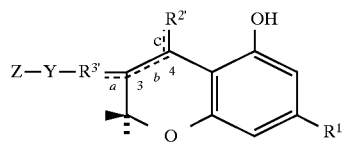

(Ia)

wherein R¹ is a linear or branched alkyl group having from 1 to 9 carbon atoms; R²' is linear or branched lower alkyl; R³' is linear or branched lower alkyl which is substituted by —O—, —CO—, —NR⁵—, —NR⁶—, —S—, —C(=NH)—, —CH=, —CH₂—; R⁵ and R⁶ are independently selected from the group consisting of H, and linear or branched lower alkyl; Y is a linking group or a bond; Z is a carrier; and a, b, and c are independently single or double bonds, provided that when b is a double bond, then a and c are not double bonds.

17. The method of claim 16 wherein the compound of formula (Ia) is

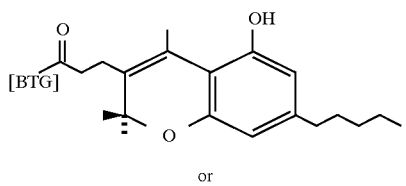

(Xa)

or

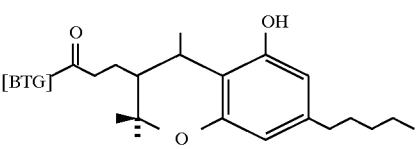

(XIIa)

18. A method for preparing antibodies to cannabinoids, the improvement comprising immunizing the host with at least one immunogen in accordance with claim 3.

19. A method for the production of an antibody useful in an assay for the detection of tetrahydrocannabinol metabolites in a biological sample comprising eliciting said antibody in the blood of a host animal by immunizing said host animal with an immunogenic compound of formula

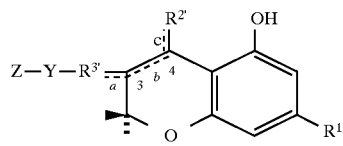

(Ia)

wherein R¹ is a linear or branched alkyl group having from 1 to 9 carbon atoms; R²' is linear or branched lower alkyl; R³' is linear or branched lower alkyl which is substituted by —O—, —CO—, —NR⁵—, —NR⁶—, —S—, —C(=NH)—, —CH=, —CH₂—; R⁵ and R⁶ are independently selected from the group consisting of H, and linear or branched lower alkyl; Y is a linking group or a bond; Z is a carrier; and a, b, and c are independently single or double bonds, provided that when b is a double bond, then a and c are not double bonds.

20. The method of claim 19 wherein the immunogenic compound is

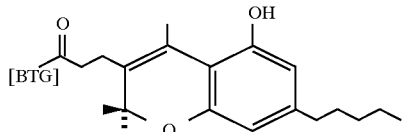

(Xa)

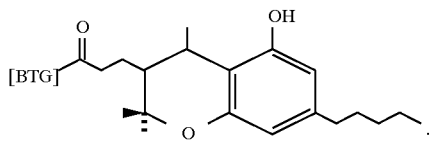
21. A test kit for the detection of tetrahydrocannabinol metabolites in a biological sample said kit comprising the antibody of claim 9.
22. A test kit for the detection of tetrahydrocannabinol metabolites in a biological sample said kit comprising the antibody of claim 11.
* * * * *

UNITED STATES PATENT AND TRADEMARK OFFICE
CERTIFICATE OF CORRECTION

PATENT NO. : 5,817,766
DATED : October 6, 1998
INVENTOR(S) : Raymond Albert Hui, Steven Mark Rosen, Salvatore Joseph Salamone It is certified that error appears in the above-identified patent and that said Letters Patent is hereby corrected as shown below:

In Claim 1, column 26, line 32, delete "a from" and insert -- from a --.

In Claim 1, column 26, line 41, insert -- or -- between formula (XV) and (XVI).

In claim 2, column 26, lines 50-65, delete formulas (X) and (XII) and insert

--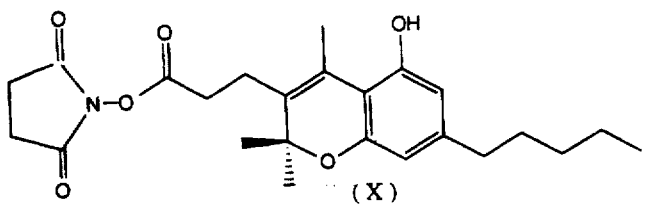

or

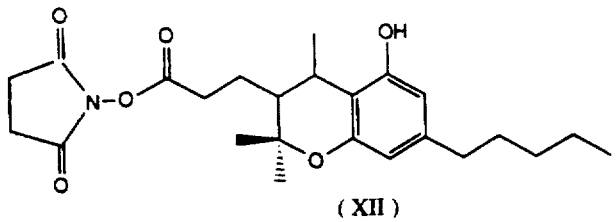

--.

In claim 4, column 27, line 24, delete "claim 7" and insert -- claim 3 --.

UNITED STATES PATENT AND TRADEMARK OFFICE
CERTIFICATE OF CORRECTION

PATENT NO. : 5,817,766
DATED : October 6, 1998
INVENTOR(S) : Raymond Albert Hui, Steven Mark Rosen, Salvatore Joseph Salamone It is certified that error appears in the above-identified patent and that said Letters Patent is hereby corrected as shown below:

In claim 8, column 27, lines 37-50, deleted formulas (Xa) and (XIIa) and insert

--

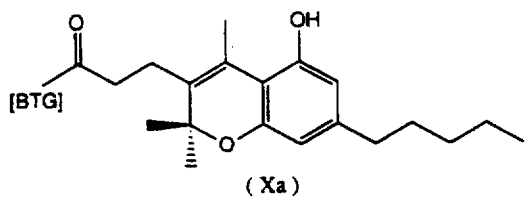

( Xa )

and

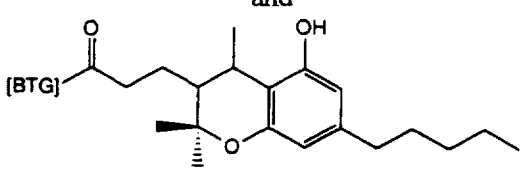

( XIIa )

--.

In claim 14, column 29, line 28, insert -- and -- between formula I(X) and (Ia).

Signed and Sealed this

Sixteenth Day of February, 1999

Attest:

*Acting Commissioner of Patents and Trademarks*

*Attesting Officer*